(12) United States Patent
Kim et al.

(10) Patent No.: US 8,758,294 B2
(45) Date of Patent: Jun. 24, 2014

(54) BALLOON INFLATION DEVICE

(75) Inventors: Robert Kim, Shoreview, MN (US);
Jiyan Liu, Maplewood, MN (US);
Thomas McPeak, Shakopee, MN (US);
Khader Mohiuddin, Medina, MN (US);
Jon Moon, Edina, MN (US); Richard A. Oftedahl, Jordan, MN (US); Norman Schwartz, Chanhassen, MN (US);
Glenn Toews, Eden Prairie, MN (US);
Robert F. Wilson, Roseville, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 1386 days.

(21) Appl. No.: 12/159,328

(22) PCT Filed: Dec. 22, 2006

(86) PCT No.: PCT/US2006/062531
§ 371 (c)(1),
(2), (4) Date: Nov. 20, 2008

(87) PCT Pub. No.: WO2007/076463
PCT Pub. Date: Jul. 5, 2007

(65) Prior Publication Data
US 2009/0312740 A1 Dec. 17, 2009

Related U.S. Application Data

(60) Provisional application No. 60/754,394, filed on Dec. 27, 2005.

(51) Int. Cl.
*A61M 29/00* (2006.01)
(52) U.S. Cl.
USPC .................. 604/99.02; 604/96.01; 604/97.01; 604/98.01; 604/99.04

(58) Field of Classification Search
USPC .................... 604/96.01–99.01, 99.02–103.14
See application file for complete search history.

(56) References Cited

U.S. PATENT DOCUMENTS

| 3,731,679 A | 5/1973 | Wilhelmson et al. |
| 3,739,943 A | 6/1973 | Wilhelmson et al. |

(Continued)

FOREIGN PATENT DOCUMENTS

| EP | 0359531 A2 | 3/1990 |
| EP | 0581708 A2 | 2/1994 |
| WO | 99/21600 A2 | 5/1999 |

*Primary Examiner* — Emily Schmidt
*Assistant Examiner* — Lauren M Peng
(74) *Attorney, Agent, or Firm* — Shumaker & Sieffert, P.A.

(57) ABSTRACT

One embodiment provides a method implemented by a powered inflation device to prepare a balloon catheter for use during a medical procedure. In this embodiment, the method includes drawing an amount of medical fluid from a fluid reservoir into the inflation device during a first motorized operation of the inflation device, removing an amount of air from the balloon catheter during a second motorized operation of the inflation device, and injecting the amount of medical fluid from the inflation device into the balloon catheter during a third motorized operation of the inflation device to inflate a balloon located at a distal end of the balloon catheter. The powered inflation device may be a stand-alone device in one embodiment. In one embodiment, the powered inflation device is coupled to an angiographic injector system. When it is coupled to an angiographic injector system, the balloon inflation device and the injector system may be controlled by a common control panel, or console, in one embodiment.

23 Claims, 19 Drawing Sheets

(56) References Cited

U.S. PATENT DOCUMENTS

| | | | |
|---|---|---|---|
| 4,512,764 | A | 4/1985 | Wunsch |
| 4,535,820 | A | 8/1985 | Raines |
| 4,559,036 | A | 12/1985 | Wunsch |
| 4,854,324 | A | 8/1989 | Hirschman et al. |
| 4,888,004 | A | 12/1989 | Williamson, IV et al. |
| 4,966,199 | A | 10/1990 | Ruschke |
| 4,966,579 | A | 10/1990 | Polaschegg |
| 5,021,046 | A | 6/1991 | Wallace |
| 5,024,668 | A * | 6/1991 | Peters et al. .................. 606/194 |
| 5,084,060 | A | 1/1992 | Freund et al. |
| 5,152,776 | A | 10/1992 | Pinchuk |
| 5,171,299 | A | 12/1992 | Heitzmann et al. |
| 5,196,017 | A | 3/1993 | Silva et al. |
| 5,226,886 | A | 7/1993 | Skakoon et al. |
| 5,249,579 | A | 10/1993 | Hobbs et al. |
| 5,254,101 | A | 10/1993 | Trombley, III |
| 5,267,964 | A | 12/1993 | Karg |
| 5,300,017 | A | 4/1994 | Isoyama et al. |
| 5,300,027 | A | 4/1994 | Foote et al. |
| 5,346,470 | A | 9/1994 | Hobbs et al. |
| 5,423,749 | A | 6/1995 | Merte et al. |
| 5,464,388 | A | 11/1995 | Merte et al. |
| 5,494,036 | A | 2/1996 | Uber, III et al. |
| 5,515,851 | A | 5/1996 | Goldstein |
| 5,569,181 | A | 10/1996 | Heilman et al. |
| 5,573,515 | A | 11/1996 | Wilson et al. |
| 5,599,301 | A | 2/1997 | Jacobs et al. |
| 5,739,508 | A | 4/1998 | Uber, III |
| 5,795,333 | A | 8/1998 | Reilly et al. |
| 5,800,397 | A | 9/1998 | Wilson et al. |
| 5,806,519 | A | 9/1998 | Evans, III et al. |
| 5,808,203 | A | 9/1998 | Nolan, Jr. et al. |
| 5,840,026 | A | 11/1998 | Uber, III et al. |
| 5,843,037 | A | 12/1998 | Uber, III |
| 5,873,861 | A | 2/1999 | Hitchins et al. |
| 5,885,216 | A | 3/1999 | Evans, III et al. |
| 5,920,054 | A | 7/1999 | Uber, III |
| 5,947,935 | A | 9/1999 | Rhinehart et al. |
| RE36,648 | E | 4/2000 | Uber, III et al. |
| 6,096,011 | A | 8/2000 | Trombley, III et al. |
| 6,099,502 | A | 8/2000 | Duchon et al. |
| 6,149,627 | A | 11/2000 | Uber, III |
| 6,197,000 | B1 | 3/2001 | Reilly et al. |
| 6,221,045 | B1 | 4/2001 | Duchon et al. |
| 6,306,117 | B1 | 10/2001 | Uber, III |
| 6,317,623 | B1 | 11/2001 | Griffiths et al. |
| 6,339,718 | B1 | 1/2002 | Zatezalo et al. |
| RE37,602 | E | 3/2002 | Uber, III et al. |
| 6,385,483 | B1 | 5/2002 | Uber, III et al. |
| 6,397,098 | B1 | 5/2002 | Uber, III et al. |
| 6,402,717 | B1 | 6/2002 | Reilly et al. |
| 6,440,107 | B1 | 8/2002 | Trombley, III et al. |
| 6,442,418 | B1 | 8/2002 | Evans, III et al. |
| 6,471,674 | B1 | 10/2002 | Emig et al. |
| 6,475,192 | B1 | 11/2002 | Reilly et al. |
| 6,520,930 | B2 | 2/2003 | Critchlow et al. |
| 6,626,862 | B1 | 9/2003 | Duchon et al. |
| 6,643,537 | B1 | 11/2003 | Zatezalo et al. |
| 6,652,489 | B2 | 11/2003 | Trocki et al. |
| 6,673,033 | B1 | 1/2004 | Sciulli et al. |
| 6,699,219 | B2 | 3/2004 | Emig et al. |
| 6,731,971 | B2 | 5/2004 | Evans, III et al. |
| 6,733,477 | B2 | 5/2004 | Cowan et al. |
| 6,743,202 | B2 | 6/2004 | Hirschman et al. |
| 6,764,461 | B2 * | 7/2004 | Mickley et al. .................. 604/15 |
| 6,790,196 | B2 * | 9/2004 | Kokate et al. .................. 604/28 |
| 6,889,074 | B2 | 5/2005 | Uber, III et al. |
| 6,901,283 | B2 | 5/2005 | Evans, III et al. |
| 6,939,302 | B2 | 9/2005 | Griffiths et al. |
| 2002/0045854 | A1 * | 4/2002 | Royo et al. .................. 604/97.03 |
| 2002/0143294 | A1 * | 10/2002 | Duchon et al. .................. 604/131 |
| 2007/0197963 | A1 | 8/2007 | Griffiths et al. |
| 2007/0213656 | A1 | 9/2007 | Ferdinand |
| 2008/0183131 | A1 | 7/2008 | Duchon et al. |
| 2009/0312740 | A1 | 12/2009 | Kim et al. |

* cited by examiner

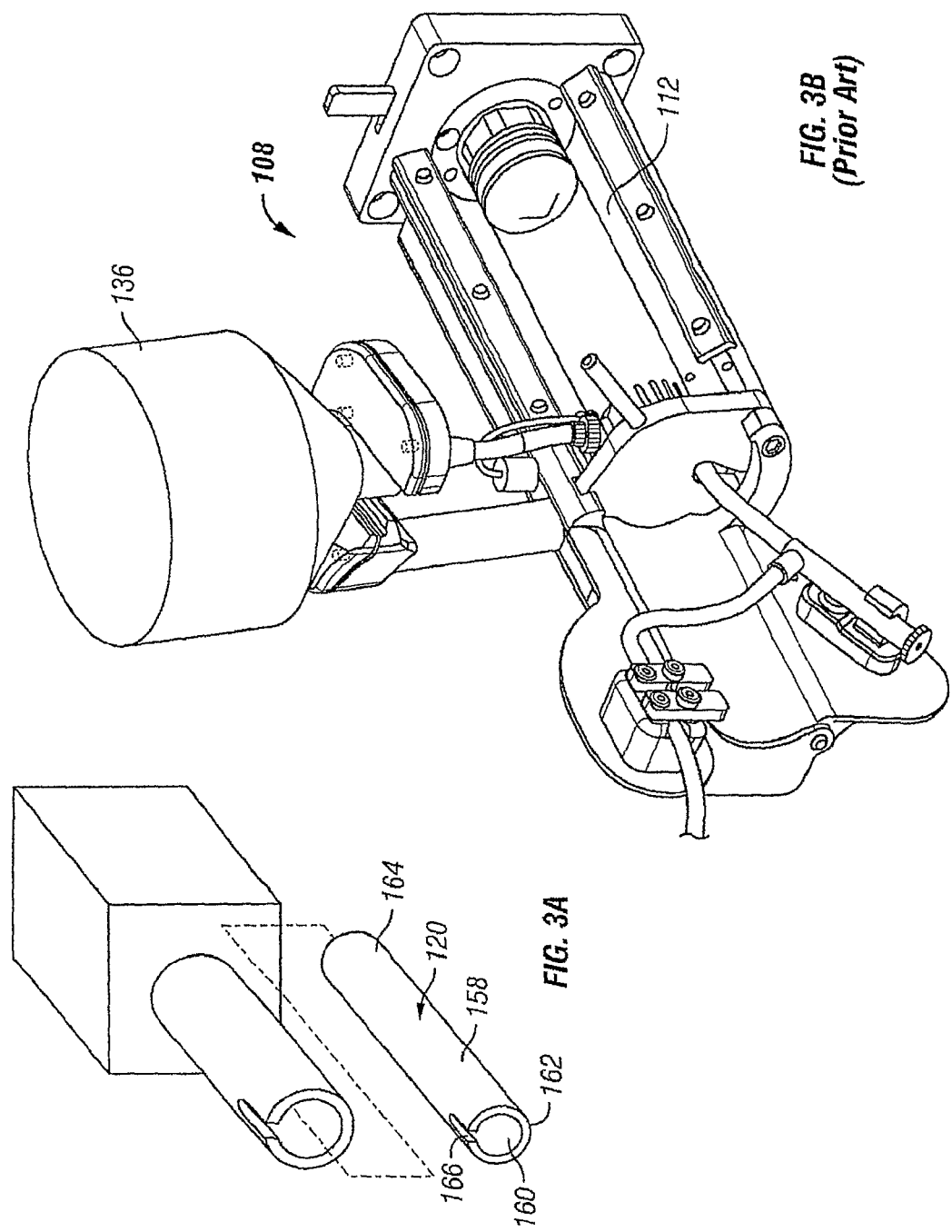

BALLOON INFLATION DEVICE

RELATED APPLICATIONS

This application is the national stage filing of corresponding international application number PCT/US2006/062531, filed Dec. 22, 2006 which claims priority to and the benefit of U.S. Provisional Application No. 60/754,394 filed Dec. 27, 2005, all of which are hereby incorporated by reference.

TECHNICAL FIELD

The present application relates generally to the use of injection devices in medical systems, and more specifically to the use of balloon inflation devices.

BACKGROUND OF THE INVENTION

Automatic injection devices, such as Applicant's device described in U.S. Pat. No. 6,099,502, are used to deliver fluids such as saline and contrast agents through a catheter to a patient. The devices typically include a motor-driven linear actuator that forces a plunger through a syringe, thereby creating a desired fluid flow into the patient. For sanitation purposes, the syringe and all associated tubing between the patient and the syringe may be disposable.

Preparing the automatic injection device for operation can be a time-consuming process. Various tubes may need to be connected together and to the device. The operator preparing the injection device for operation must often be careful to ensure that the connections are tight and that none of the tubes are pinched or otherwise blocked. Furthermore, during the assembly process, the operator will prime various subassemblies with saline and contrast before connecting them to other subassemblies. Priming is done to prevent air from being introduced into the patient. In certain cases, intermittent priming steps are performed so that fluid-to-fluid connections may be made at predetermined assembly steps. The ends are then connected together, thereby merging menisci and minimizing the chance that air is introduced into the connection.

Once set-up is complete, the physician positions a catheter and inserts it into the patient. The use and type of the catheter varies depending on the procedure being performed. For example, the catheter may be used to deliver contrast agents, using the aforementioned injection device, or to provide a guide for routing ultrasonic imaging probes or balloon devices.

Some of the devices require fluid flow, such as the balloon devices, and are connected to special manual syringes. These special syringes are often called "inflators" (or inflation devices) and use a plunger that is manually advanced using a rod that is threaded into a handle to allow the operator to advance the plunger using very small, controlled increments. However, these threads also give the physician such a mechanical advantage as to possibly take away the "feel" of the balloon inflation. Thus, the physician cannot typically feel the effect that the balloon may be having on the wall of the vessel that it is stretching against. For example, the physician may not be able to feel a calcium deposit cracking. The special syringes typically include a pressure gauge, but the gauge is often located on the syringe itself, and it therefore may be impractical for the physician to monitor the gauge as he or she tries to also watch an image of the balloon being inflated on a monitor.

In addition, physicians typically need to manually prime these types of inflation devices, along with the corresponding balloon catheters that are to be used. For instance, a physician may need to manually prime the inflation device by first filling the device with an amount of fluid, such as a mixture of contrast and saline. The physician may then purge a small amount of this fluid from the inflation device to remove air, or the physician may also aspirate air from the inflation device by coupling it to a manual syringe. The physician also needs to aspirate air from the balloon catheter. To do so, the physician may use a manual syringe. Once the inflation device and the balloon catheter are primed, the physician may then connect these components together. The physician may use a stopcock during the priming procedure. The stopcock is coupled to the inflation device, the manual syringe, and the balloon catheter. The manual priming of the inflation device and the balloon catheter, however, may somewhat burdensome and time-consuming to the physician if he/she needs to do such priming multiple times during a given patient procedure or during a given day.

SUMMARY OF THE INVENTION

It would be therefore advantageous to use a balloon inflation device that at least partially automates the priming procedure, according to one embodiment. The balloon inflation device may be a stand-alone device, or it may be coupled to an angiographic injector system. When it is coupled to an angiographic injector system, the balloon inflation device and the injector system may be controlled by a common control panel, or console, in one embodiment.

In one embodiment, a balloon inflation device is provided. In this embodiment, the balloon inflation device is coupled to a balloon catheter and is configured to auto-prime the device and catheter assembly. One embodiment provides a method implemented by a balloon inflation device to prepare a balloon catheter for inflation. In this embodiment, the method includes filling the balloon inflation device with an amount of liquid during a first motorized operation, and aspirating an amount of air from the balloon catheter during a second motorized operation to prepare the balloon catheter for inflation. A user of the inflation device may specify a desired vacuum pressure limit for the catheter that is to be achieved prior to inflation. In one embodiment, the balloon catheter may be inflated or deflated after it has been prepared by the inflation device. A timer coupled to the inflation device may be used to time individual inflation periods, and a graphical user interface provided by the inflation device may display pressure-volume curve characteristics for individual inflations.

The details of one or more embodiments of the invention are set forth in the accompanying drawings and the description below. Other features, objects, and advantages will be apparent from the description and drawings, and from the claims.

BRIEF DESCRIPTION OF THE DRAWINGS

FIG. 3A is a perspective view of an adapter sleeve, useable to convert an injector system into an embodiment of a balloon inflation device of the present invention.

FIG. 3B is a perspective view of a prior art injector subassembly of an automatic injection device.

DETAILED DESCRIPTION

Figure 1:
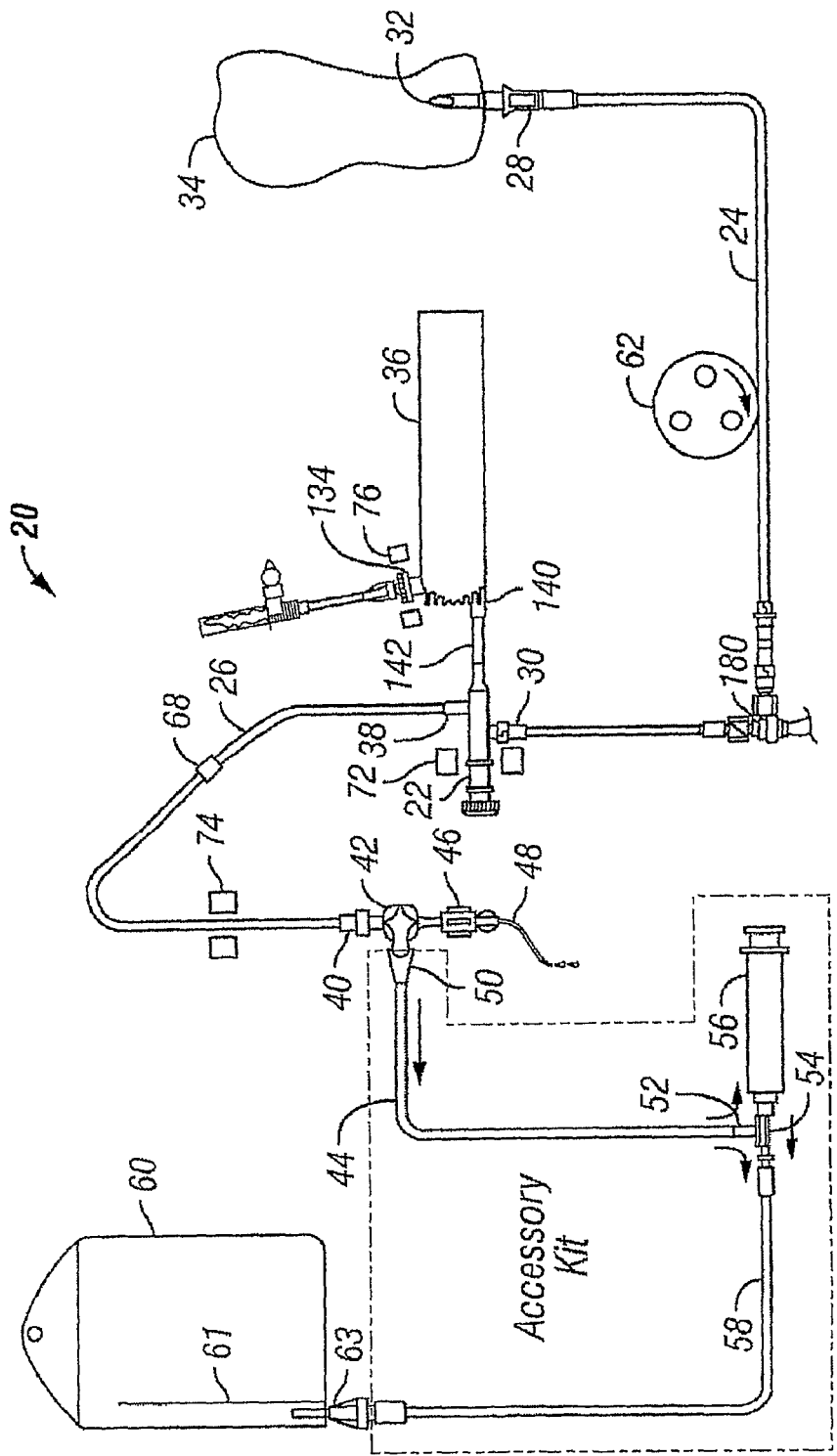
FIG. 1 is a diagrammatic representation of an embodiment of the fluid network of the present invention.

Referring now to the Figures, and first to FIG. 1, there is shown a fluid network 20 comprising a disposable patient manifold 22 connected to a saline line 24 and an output line 26. The saline line 24 has a first end 28 and a second end 30. The first end 28 is connected to a bag connector 32, useable to establish fluid communication between the line 24 and a saline bag 34.

The patient manifold 22 is also connected to a syringe 36 of an automatic injection device (not shown) for receiving the fluid ejected therefrom. The patient manifold 22 is thus useable to selectably connect the output line 26 with either the saline line 24 or the syringe 36. The patient manifold 22 may be any device capable of selectively directing flow between at least three ports, such as a three-way check valve, a manual or automatic three-way stopcock, a motor operated valve, or a collection of check valves operably disposed within the appropriate lines to effect the desired flow directions. Preferably, the patient manifold 22 comprises an automatic valve that is constructed and arranged such that fluid communication normally exists between the saline line 24 and the output line 26. However, when a predetermined amount of positive fluid pressure is generated by the syringe 36, the fluid pressure causes the fluid communication between the saline line 24 and the output line 26 to become blocked, and opens fluid communication between the syringe 36 and the output line 26. An example of this type of patient manifold is the spring-loaded spool valve described in U.S. patent application Ser. No. 09/542,422, incorporated by reference herein in its entirety. To provide controlled saline pressure when the patient manifold 22 is aligned to deliver saline to the output line 26, the saline line 24 is fed through a pump, such as a peristaltic pump 62, of the automatic injection device.

The output line 26 is connected at a first end 38 to the patient manifold 22 and at a second end 40 to a three-way stopcock 42. The three-way stopcock 42 may be manually or automatically operated and is also connected to a waste line 44 and a catheter connector 46 such that it may be used to align the output line 26 with either a catheter 48 or the waste line 44.

The waste line 44 has a first end 50 connected to the three-way stopcock 42 and a second end 52 connected to a three-way check valve 54. The three-way check valve 54 is also connected to an auxiliary syringe 56 and a bag line 58. The three-way check valve 54 is constructed and arranged so that the auxiliary syringe 56 may be used as a hand pump. When the wiper of the syringe 56 is withdrawn, the check valve 54 blocks the bag line 58 and directs fluid from the waste line 44 into the syringe 56. When the wiper is then advanced, the check valve 54 blocks the waste line 44 and directs fluid from the syringe 56 into the bag line 58. The bag line 58 is connected to a waste bag 60 where the waste fluid is deposited. When the syringe 56 is used to aspirate saline into the waste bag 60, it is important that the saline line 24 is not compressed and occluded by the peristaltic pump 62.

Figure 2:
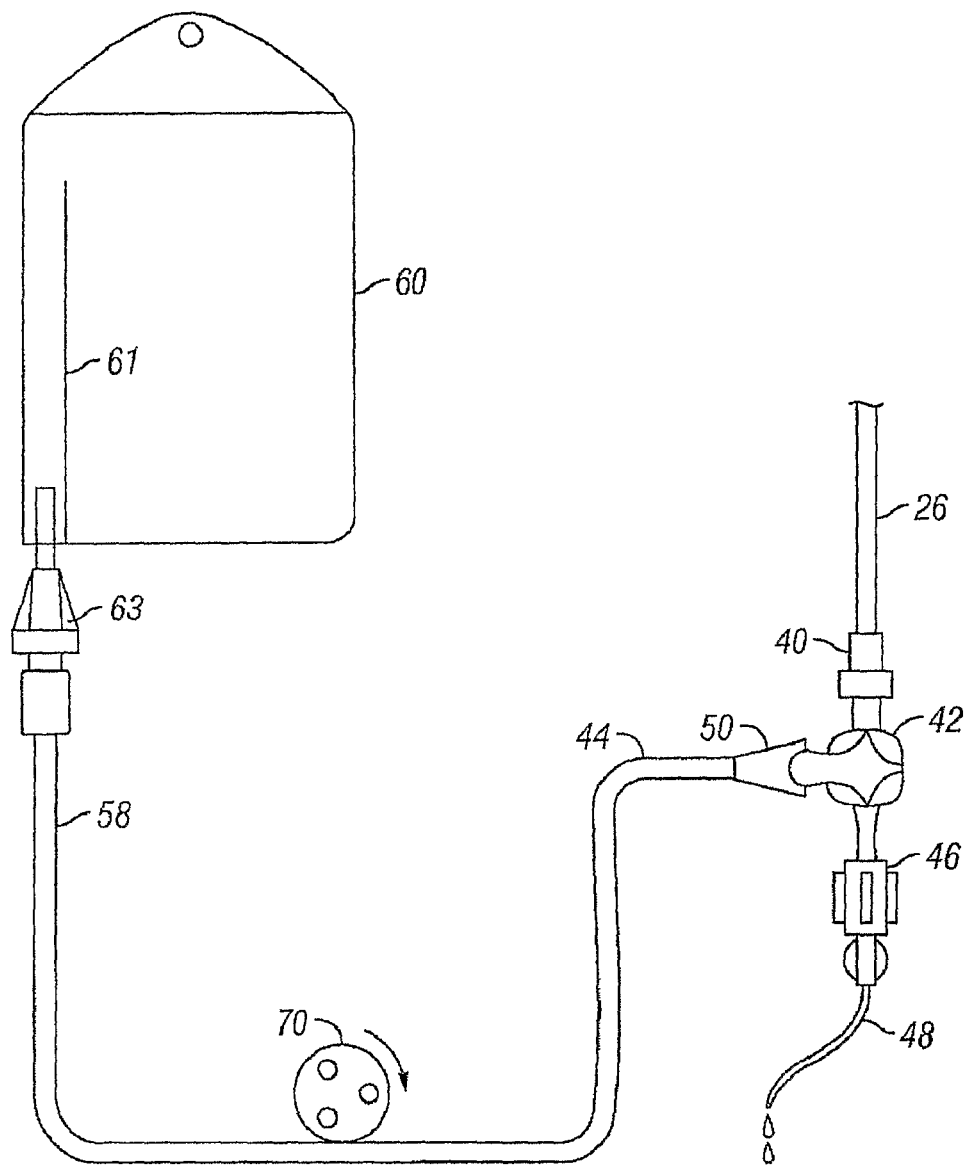
FIG. 2 is a diagrammatic representation of an alternative embodiment of the fluid network of the present invention.

Alternatively, as seen in FIG. 2, an automatic pump 70 may be used to pump liquid to the waste bag 60. The automatic pump 70 is shown as a peristaltic pump that acts on the waste line 44. As peristaltic pumps act on the outside of a tube, the waste line 44 and the bag line 58 are integral.

The fluid network 20 is thus designed to be attached to an automatic injection device quickly and to be primed with little or no human interaction. The fluid network 20 is assembled, packaged and sterilized so that it may be shipped as a completely assembled kit. The waste bag 60 may double in function as the packaging bag in which all of the aforementioned components of the fluid communication network 20 are shipped. This eliminates the need for a separate packaging bag, an added expense. A divider 61 is integrated, such as by heat sealing, into the bag to limit the amount of fluid that could spill from the bag 60 in the event of a leak developing around the connection 63 between the bag 60 and the bag line 58.

In use, the fluid network 20 is removed from its packaging and the patient manifold 22 is connected to the syringe of the automatic injection device. The saline line 24 is threaded through the peristaltic pump 62 and verification is made that the three-way stopcock 42 is aligned to the waste line 44. Next, the bag line 58 is connected to the waste bag 60 and the saline line 24 is connected to the saline bag 34.

The fluid network 20 is now ready for priming. The automatic injection device, such as the device 102 shown in FIG. 3 and discussed in more detail below, includes a computer 106 having a program segment for instructing the device 102 to enter a priming mode. When selected, the priming mode program segment includes a command that causes the computer 106 to align the patient manifold 22 for contrast agent, or if the patient manifold 22 is a manually operated valve, displays a message instructing the operator to do so. The program segment prevents further action unless the computer 106 receives verification from the operator that the manifold 22 is aligned. A patient manifold position detector 72 is operably connected to the manifold 22 and in communication with the computer 106, obviating the need for verification from the operator. Once the position of the manifold 22 is verified, either by operator input or with the detector 72, the program segment causes the computer 106 to send a signal to the linear actuator of the automatic injector that advances the plunger of the syringe 36 slightly to force potential air bubbles from the syringe connecting tube 66, which connects the patient manifold 22 to the syringe 36. Any air bubbles in the connecting tube 66 are forced into the output line 26.

The priming program segment 64 then aligns the patient manifold 22 for saline. After manifold position detector 72 verifies that the patient manifold 22 is aligned for saline, the peristaltic pump 62 is activated for a predetermined interval. The interval is long enough, for a given pump speed, to fill the saline line 24, the patient manifold 22 and the output line 26 with saline.

The peristaltic pump 62 may operate in a priming mode whereby it turns in a stutter fashion to send pressure pulses through the various lines. These pressure pulses act to dislodge air bubbles from the inner walls of the lines, thus obviating the need for the operator to tap on the lines during the priming procedure. To monitor for the presence of bubbles, a bubble detector 74 is placed in one or more locations and are electrically connected to the computer of the automatic injector. In priming mode, detection of bubbles is expected. However, when the injector is in injection mode, the receipt of a signal from the bubble detector(s) 74 will cause the injector to stop forward movement of the plunger of the syringe 36. The waste bag 60 eventually receives all of the priming fluid.

Alternatively, if a syringe pump (not shown) is used instead of a peristaltic pump 62, the syringe may be operated by a linear actuator in a stutter fashion such that the linear actuator intermittently hammers on the plunger of the syringe thereby creating the necessary pressure pulses to dislodge air bubbles from the inner walls of the various lines. One skilled in the art will see that any pump substituted for the peristaltic pump 62 can be operated in an on and off fashion to create such pressure pulses.

Priming having thus been completed, the attending physician may insert the catheter 48 into the target blood vessel and attach the catheter 48 to the fluid communication network 20 using the catheter connector 46. The catheter 48 is then primed, and proper placement within the vessel is verified, by taking a suction on the catheter 48 until blood appears in the clear tubing of the output line 26. Taking suction on the catheter 48 is performed by aligning the stopcock 42 to establish fluid communication between the output line 26 and the catheter 48. Suction may then be drawn on the output line 26 by retracting the plunger of the syringe 36, or reversing the rotation of the peristaltic pump 62. However, it may be undesirable to establish reverse fluid flow into the syringe 36 or the saline bag 32. Doing so prevents reuse of the saline remaining in the saline bag 34 and reuse of the contrast agent in the syringe 36. The output line 26 may also include a disconnect 68 that allows the physician to connect a hand syringe to the output line 26 and take a suction thereon. Once blood appears in the clear output line 26, the disconnect 68 is reconnected and the three-way stopcock 42 is aligned to the waste line 44. The peristaltic pump 62 is then run in a forward direction to force the blood from the output line 26, through the stopcock 42, and into the waste line 44. The waste bag 60 receives the blood and other waste fluids for safe containment and easy disposal.

Figure 3:
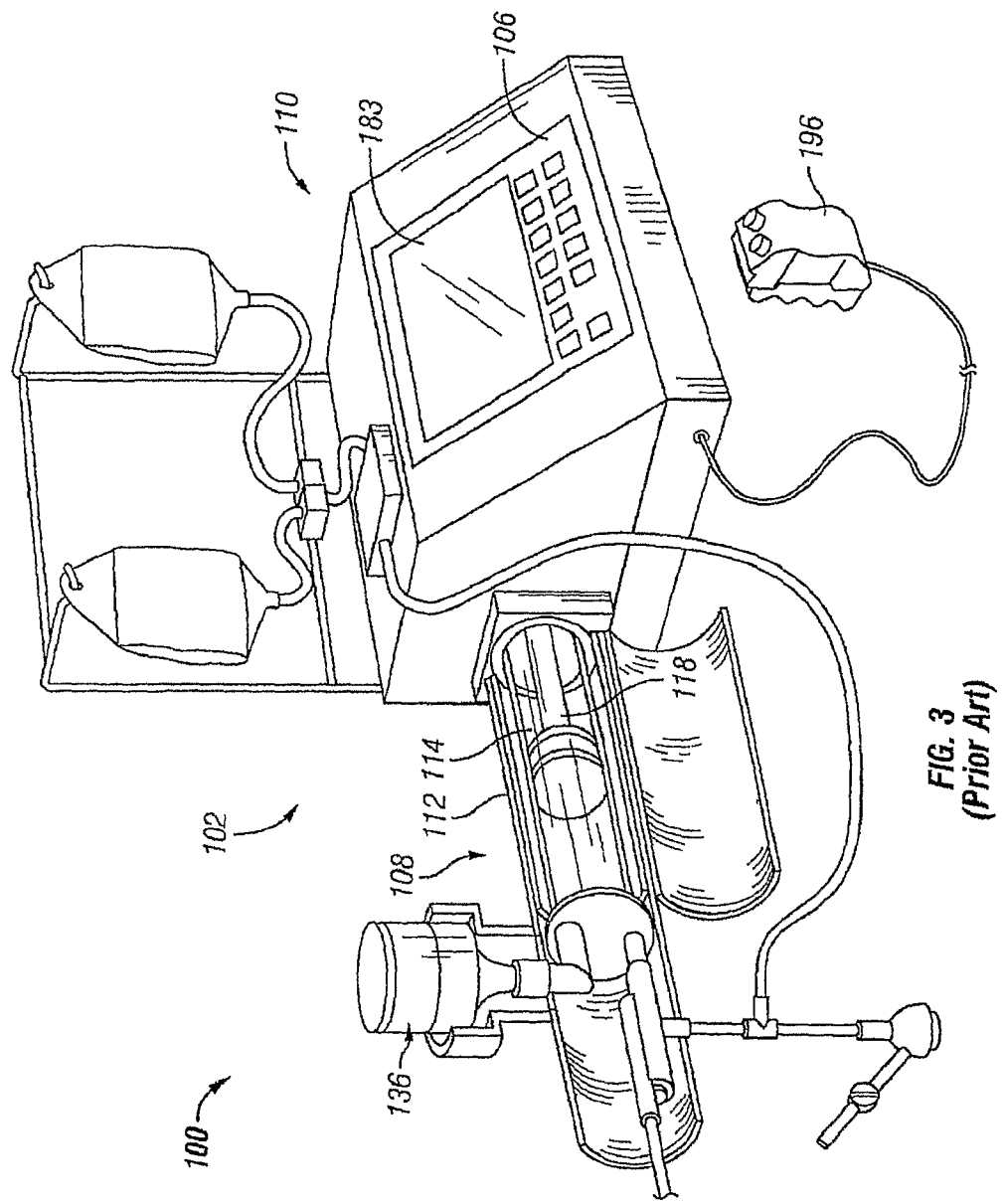
FIG. 3 is a perspective view of a prior art injector system that is convertible to an embodiment of a balloon inflation device of the present invention.

Referring now to FIGS. 3, 3A, and 3B, another embodiment of the present invention provides an automatic balloon inflation device 100. This embodiment of the balloon inflation device 100 is constructed and arranged to allow an existing automatic injection device 102, such as the CL100 made by Acist Medical Systems, Inc. of Eden Prairie, Minn. and described in U.S. Pat. No. 6,099,502 incorporated by reference herein in its entirety. It is understood by one skilled in the art that a separate balloon inflation device could be constructed using the devices and techniques represented herein combined with the necessarily associated functionality of existing angiographic injectors.

The automatic injection device 102 is converted into a balloon inflation device 100, when it is accessorized to accept a small, balloon inflation syringe 104 (FIGS. 6 and 7), and when the computer 106 of the injection device 102, is updated with a program that allows the injection device 102 to operate in "Inflation Mode".

Figure 4:
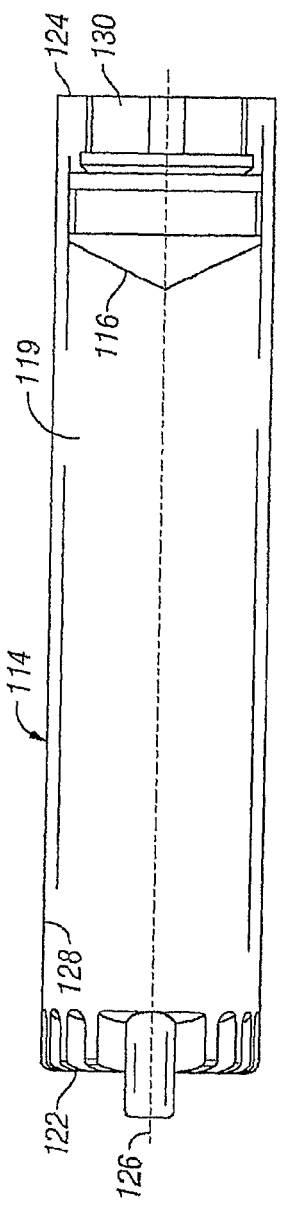
FIG. 4 is bottom view of a prior art syringe insertable into an injector system.
Figure 5:
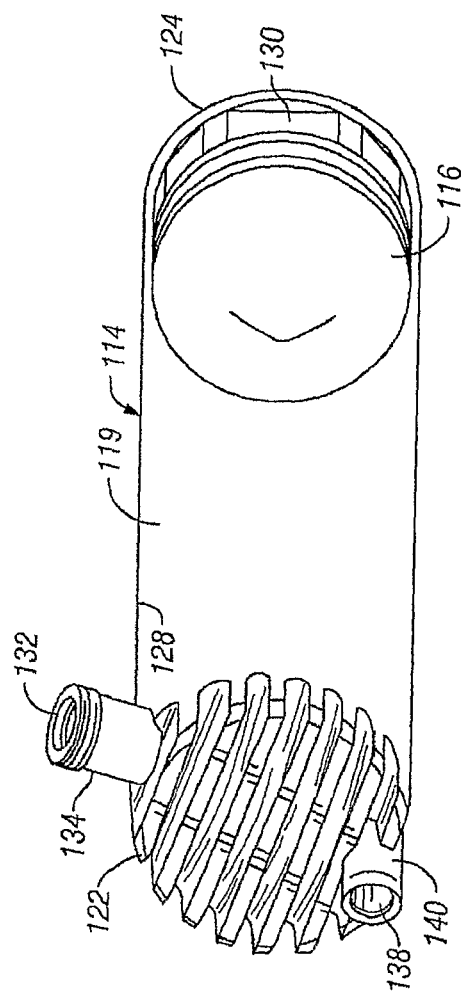
FIG. 5 is a perspective view of the prior art syringe of FIG. 4.

The example of an automatic injection device 102 shown in FIG. 3 includes an injector subassembly 108 and a user-interface subassembly 110. The injector subassembly 108 includes a syringe holder 112, typically used to house a relatively large syringe body 114 having fluid capacities on the order of 10 cc to 250 cc, such as those used for angiography and shown in FIGS. 4 and 5. The syringe body 114 is equipped with a plunger 116, slideably disposed therein. The plunger is acted upon by a linear actuator 118 (FIG. 3) of the injector subassembly and is removably attached thereto. The particular angiography syringe body 114 shown in FIGS. 4 and 5 is fully described in U.S. Pat. No. 6,099,502 (incorporated by reference herein) and includes features for use in an automatic injection device, the injector subassembly of which is shown in FIG. 3B. These features are discussed briefly herein as they provide examples of injector-specific considerations that are made in the design of a conversion kit to allow the injector 102 to be used as a balloon injector 100. These features may also be incorporated into the design of a balloon inflation syringe 104.

Thus, the angiography syringe 114 includes a wall 119 defining first and second opposite ends 122, and 124. The first end 122 corresponds to a distal end of the syringe 114, and the second end 124 corresponds to a proximal end of the syringe 114. The wall 119 of the syringe 114 is cylindrical in the illustrated embodiment and includes a central axis 126 extending longitudinally therethrough.

The syringe body 114 defines a pumping chamber 128 in an interior thereof. A wiper or plunger 116 is located in the pumping chamber 128 and is constructed and arranged for reciprocal motion between a position adjacent to the first end 122 and the second end 124. That is, when the syringe 114 is mounted in a system analogous to the angiographic system 102, the linear actuator 118 from the system energizes the plunger 116 and causes it to move between the second end 124 and the first end 122. A plunger support member 130 supports the plunger 116. The support member 130 preferably comprises a rigid, hard material, for example, a polycarbonate or ABS plastic, to interface between an actuator 118 and the plunger 116. The member 130 attaches to the plunger 116 by a snap fit, a magnetic fit, or a similar quick attach coupling that allows the plunger 116 to be pushed and pulled.

The syringe 114 defines at least one port for providing fluid flow communication with the pumping chamber 128. In the particular embodiment illustrated, the syringe 114 includes two ports providing fluid flow communication with the pumping chamber 128. Specifically, an inlet port 132 allows the pumping chamber 128 in the syringe 114 to be filled with contrast material, and purged of air through the inlet port 132. A housing 134 circumscribes the inlet port 132 and allows the inlet port 132 to be connected with an appropriate bottle or bag 136 (FIGS. 3 and 3B) of contrast agent or saline. When the syringe 114 is oriented in a syringe holder 112 in an angiographic system as described above, the inlet port 132 is located above the pumping chamber 128.

The inlet port housing 134 is preferably clear because one aspect of the present invention provides a fluid detection device 76 (FIG. 1) that is preferably operably connected to the housing 134. The device ensures that all air has been purged from the syringe 114 and that fluid occupies the housing 134. The fluid detection device may be embodied in a passive coating on the interior surface of the syringe that reacts when contacted by a fluid. Alternatively, the device may be embodied using, for example, an ultrasound, optic, or electromagnetic emitter to detect the presence of fluid in the housing 134. One embodiment provides an optic sensor used to determine the position of a floating ball of a floating ball valve. When the ball is supported by fluid in an up position, any air in the syringe 114 has been purged. Though the syringe 114 shown in FIGS. 4 and 5 is denoted as prior art, as mentioned above, the fluid detection device 76 is considered a novel aspect of the present invention.

In this embodiment, the syringe 114 is mounted in an angiographic system at an angle such that any air bubbles present in the pumping chamber 128 migrate toward the inlet port 132, through which they may be purged. To purge air through the inlet port 132, the inlet port housing 134 houses a valve assembly that permits air to be expelled or purged from the syringe 114, but does not allow fluid to flow out of the pumping chamber 128 and back into the bottle 136 of contrast fluid when pressure movement is applied on the syringe side of the check valve. Such a check valve is described in U.S. Pat. No. 6,099,502, which is incorporated by reference herein.

The syringe 114 also includes an outlet port 138 in fluid flow communication with the pumping chamber 128. The outlet port 138 permits fluid flow from the pumping chamber 128 to a fluid communication network, such as fluid network 20. The outlet port 138 is surrounded, or circumscribed, by an outlet port housing 140 extending, or projecting, from the end wall of the syringe 114. The outlet port housing 140 is constructed and arranged to receive a patient manifold connector tube 142 (FIG. 1).

The syringe body 114 is too large for use as a balloon inflation syringe. However, the syringe holder 112 is constructed and arranged specifically to hold a particular syringe body 114. Thus, to place a balloon inflation syringe in the syringe holder and provide proper alignment with relation to the linear actuator 118, and provide the necessary support needed to operate a relatively thin-walled balloon inflation syringe with a powerful linear actuator 118, the present invention provides an adapter sleeve 120, shown in FIG. 3A and in phantom in FIG. 6, constructed and arranged with outer dimensions that allow the sleeve 120 to be properly cradled by the syringe holder 112. The inside cavity of the adapter sleeve is configured to closely mate with a balloon inflation syringe 104.

The balloon inflation syringe 104 may be closely analogous to the angiographic syringe 114, to allow attachment of the balloon inflation syringe 104 to the injector subassembly 108. Thus, the balloon inflation syringe 104 includes a wall that defines a pumping chamber 146 therein that is an appropriately small size to allow controlled balloon inflation, typically on the order of 5 ml to 40 ml. The syringe 104 also includes a plunger 148 that attaches to the linear actuator 118 in the same manner as the plunger 116 of the syringe 114. An inlet port 150, defined by an inlet port housing 152, establishes fluid communication between the supply bottle 136 and the pumping chamber 146. The inlet port housing 152 is longer than the analogous inlet port housing 134 of the angiographic syringe 114 to allow for the smaller diameter of the balloon inflation syringe 104. An outlet port 154 defined by an outlet port housing 156, establishes fluid communication between the patient manifold connector 142 and the pumping chamber 146 of the balloon inflation syringe 104.

Similar to the ports 132 and 138 of the angiographic syringe 114, described above, the inlet port 150 and the outlet port 154 of the balloon inflation syringe 104 are located in upper portions and lower portions of the syringe 104, respectively, when the syringe 104 is loaded into the injector system 100. However, as much less fluid is being injected, and it is very rare to inject all of the fluid located in the pumping chamber 146 during a balloon inflation procedure, there may be less importance placed on the location of the ports 150 and 154. For example, the balloon inflation syringe 104 may be supplied pre-loaded with fluid, obviating the need for an inlet port 150. Further, the outlet port 154 may be more conventionally located along a central axis of the syringe 104, so long as the particular injection device 100, to which the adapter sleeve 120 is designed, accommodates the placement of the outlet port 154.

Figure 6:
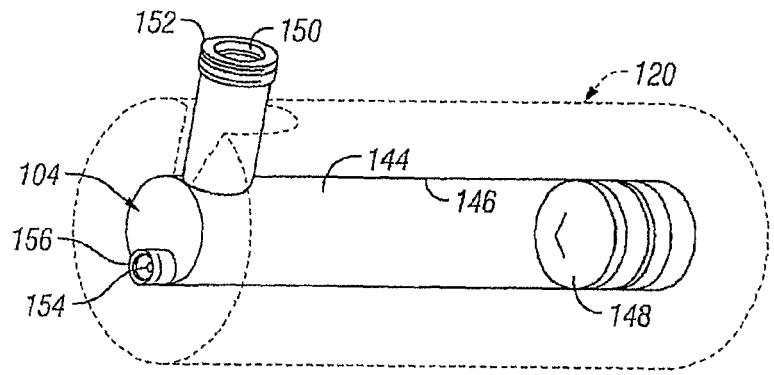
FIG. 6 is a perspective view of a syringe of the present invention surrounded by an adapter sleeve of the present invention shown in phantom lines.

Referring again to FIGS. 3A and 6, the adapter sleeve 120 is described in greater detail. The adapter sleeve 120 has an outer wall 158 defining an inner cavity 160 having an inside diameter substantially equal to the outside diameter of the balloon inflation syringe 104. The outer wall 158 is open at a first end 162 and a second end 164 such that the balloon inflation syringe 104 may be loaded into the first end 162 and so that the linear actuator 118 may act on the plunger 148 of the syringe 104 through the second end 164. The outer wall 158 also defines a groove 166 at the first end 162 that is constructed and arranged to accept the inlet port housing 152. FIG. 6 shows that when the syringe 104 is mated with the sleeve 120, the size and shape of the resulting assembly is substantially the same as the size and shape of the angiographic syringe 114.

Figure 7:
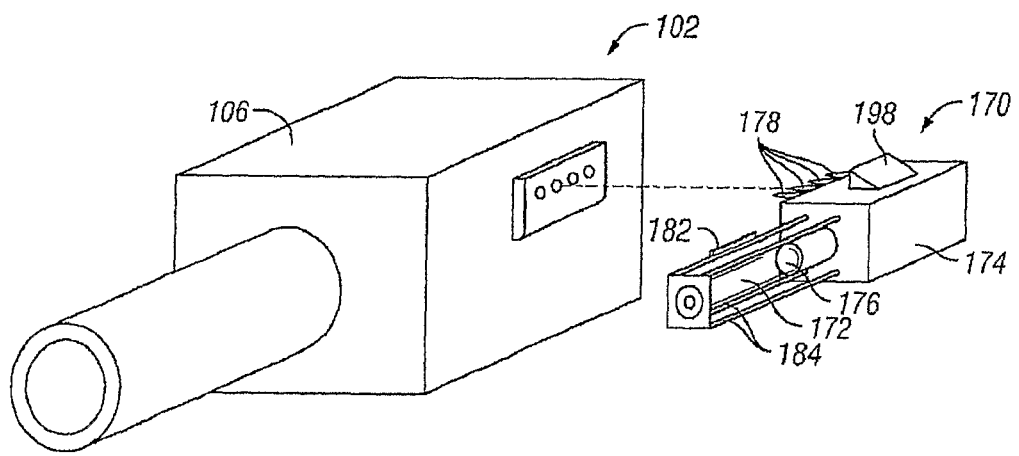
FIG. 7 is an embodiment of a balloon inflation device of the present invention.

FIG. 7 shows an alternative embodiment of a balloon inflation device 170. The balloon inflation device 170 is a unit that is attachable to an automatic injection device 102. This arrangement obviates the need for switching syringes and inserting adapter sleeves when transitioning from a diagnostic imaging procedure to a balloon catheter procedure. Additionally, providing the balloon inflation device 170 as the shown unit allows for the use of common electronics and controls to be used for supplying power and commands to the mechanical components of the device 170.

The balloon inflation device 170 includes an appropriately sized syringe 172 operably attached to a linear actuator module 174. The linear actuator module 174 contains an actuating device, such as a motor or hydraulic or pneumatic piston, useable to move a plunger 176 slideably disposed within the syringe 172.

The linear actuator module is able to receive and respond to commands given by the computer 106 of the automatic injection device 102, and receive the necessary power to drive the actuating device, through connector pins 178.

An advantage to providing a computer driven balloon inflation device, such as balloon inflation device 100 or 172, is that the device can become integrated into a closed feedback loop that can be used to accurately achieve desired pressures within a balloon catheter during an inflation procedure. Referring back to FIG. 1, there is shown a pressure transducer 180 located within the fluid communication network 20 on the saline line 24. The pressure transducer 180 is a sensitive instrument, capable of measuring small changes in pressure, such as those pertaining to biological patient attributes. Locating the pressure transducer 180 on the saline line 24 allows the patient manifold 22 to be used to insulate the transducer 180 from any high pressures that may be generated by the syringe 36.

A pressure sensor, such as the strain gauge 182, shown in FIG. 7, can be used for high pressures, such as those developed by the balloon inflation syringe 104. The strain gauge 182 is mounted to one of four syringe support rods 184 that are used to fix the syringe 172 to the linear actuator module 174. Balloon pressure may be accurately determined by measuring the amount of strain encountered by the support rods 184 as the plunger 176 is depressed. Alternatively, pressure may be measured as a function of the load placed on the linear actuator module 174. For example, if a DC motor is used to drive the linear actuator of the module 174, a circuit may be incorporated into the electronics driving the motor that is constructed and arranged to measure motor torque as a function of current drawn.

The feedback loop is formed by measuring balloon pressure and providing it to the computer 106, which then uses it to increase or decrease the amount of pressure it instructs the linear actuator module 174 or linear actuator 118 to place on the plunger 176 or 148, respectively. A significant advantage to forming a computerized feedback loop is the ability to load a program segment into the memory of the computer 106 that provides a target map to be used by the computer 106 for calculating error and determining corrective action. Another program segment can be used to create a display of target pressure and actual pressure, either numerically or graphically.

Figure 8:
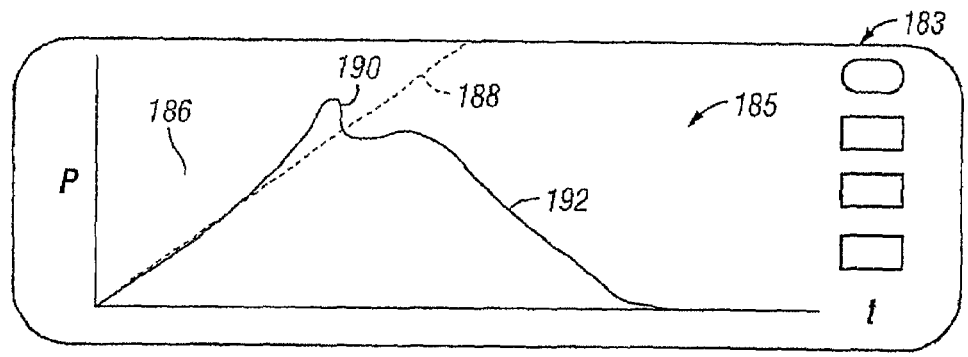
FIGS. 8-10 are examples of pressure graphs shown on a display in one embodiment of the present invention during balloon inflation procedures.
Figure 9:
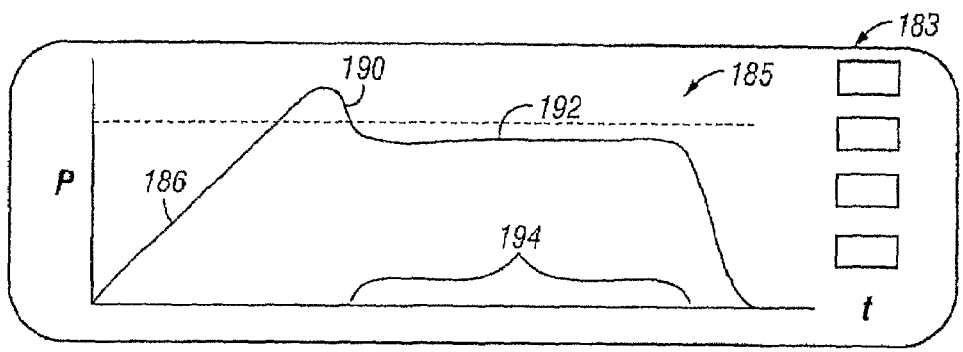
Figure 10:
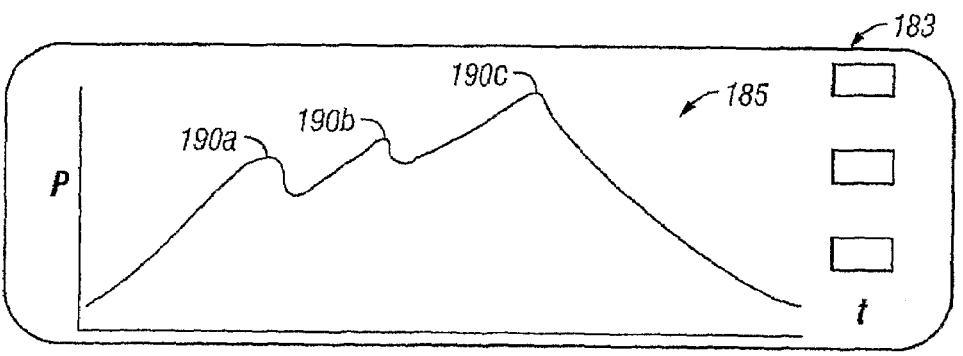

Referring now to FIGS. 8-10, there are provided examples of displays 183 showing pressure versus time graphs 185 (units and values have been omitted but are understood to be included in an actual display). A similar graph may be provided for balloon volume versus time (not shown). All such displays may be provided for a stand-alone balloon inflation device or for an inflation device that is operatively coupled to an injector system.

FIG. 8 shows a display 183 with a graph 185 that may represent a typical balloon inflation pressure profile when a balloon is used to dilate an area in a blood vessel that has become restricted due to a build-up of plaque. At 186, the balloon is inflating and pressure is rising steadily as the fluid meets with increasing resistance from the balloon and the walls of the vessel. The dotted line 188 represents the particular inflation characteristics of the balloon catheter being used in the procedure. This will be discussed in more detail below.

Typically during this procedure, there will be a sudden drop in pressure 190. This is known as a "pop" and it represents the plaque buildup giving way, the ultimate goal of the procedure. By breaking the bonds that hold the plaque together, the vessel is allowed to return to a diameter closer to that of its original size. When a balloon is being inflated manually, the physician pays attention to feeling this "pop" in the syringe being used to inflate the balloon. With the feedback loop of the present invention, a program segment is provided that allows the computer 106 to sense this "pop" and take a desired action thereafter. The graph in FIG. 8 shows that the desired action in this case was to deflate the balloon at 192.

FIG. 9 shows a similar graph 185. However, in this case, the desired action after the "pop" at 190 is to hold the pressure in the balloon constant at 192 for a predetermined period of time 194. The feedback loop is thus used to move the plunger 176 or 148 appropriately to maintain a constant pressure in the balloon.

It is not uncommon to encounter a clot that may be broken more than once as a balloon catheter stretches it. FIG. 10 shows a graph 185 where a plurality of "pops" are encountered at 190a, 190b, and 190c. Here the program segment loaded into the computer 106 either specified a maximum pressure to be achieved, or a maximum volume to be achieved, given the pressure and volume limits of the balloon and/or the size constraints of the vessel. Alternatively, the program segment allows the device to be used in a manual mode, with safety limits set on pressure and volume. In manual mode the physician uses a hand control 196 (FIG. 3) to control the inflation of the balloon, while viewing the display 183 for visual indication of the occurrence of a "pop" at 190. Additional stimuli may be provided to the physician such as a tactile feedback mechanism, such as a vibration or a proportional force feedback, in the hand control 196, or an audible tone provided by a speaker in the monitor 183. Additionally, a program segment may be provided that allows a physician to inflate the balloon manually, while "recording" flow rates, volumes and pressures used, so that the computer 106 may "learn" how the physician inflated the balloon. The physician may then instruct the computer 106 to repeat the inflation techniques he or she just performed. There are many instances where multiple inflations must be performed and this feature allows the physician to replicate a desired inflation automatically.

FIG. 8 shows a dotted line 188 that represents a baseline pressure profile of a particular balloon catheter in a no-load environment. One aspect of the present invention provides a bar code reader 198 (FIG. 7), or other data input device, that is useable to input a pressure profile or other information about a balloon catheter. The balloon catheter manufacturer supplies the profile of the baseline no-load inflation characteristics of the balloon catheter contained therein via a bar code or other means of providing the data on or with the catheter packaging.

Knowing the baseline pressure characteristics of the balloon catheter allows the physician to view the difference between the actual, loaded pressure plot and the baseline graph 188. The difference is attributed to the resistance to inflation exhibited by the blood vessel.

Figure 11:
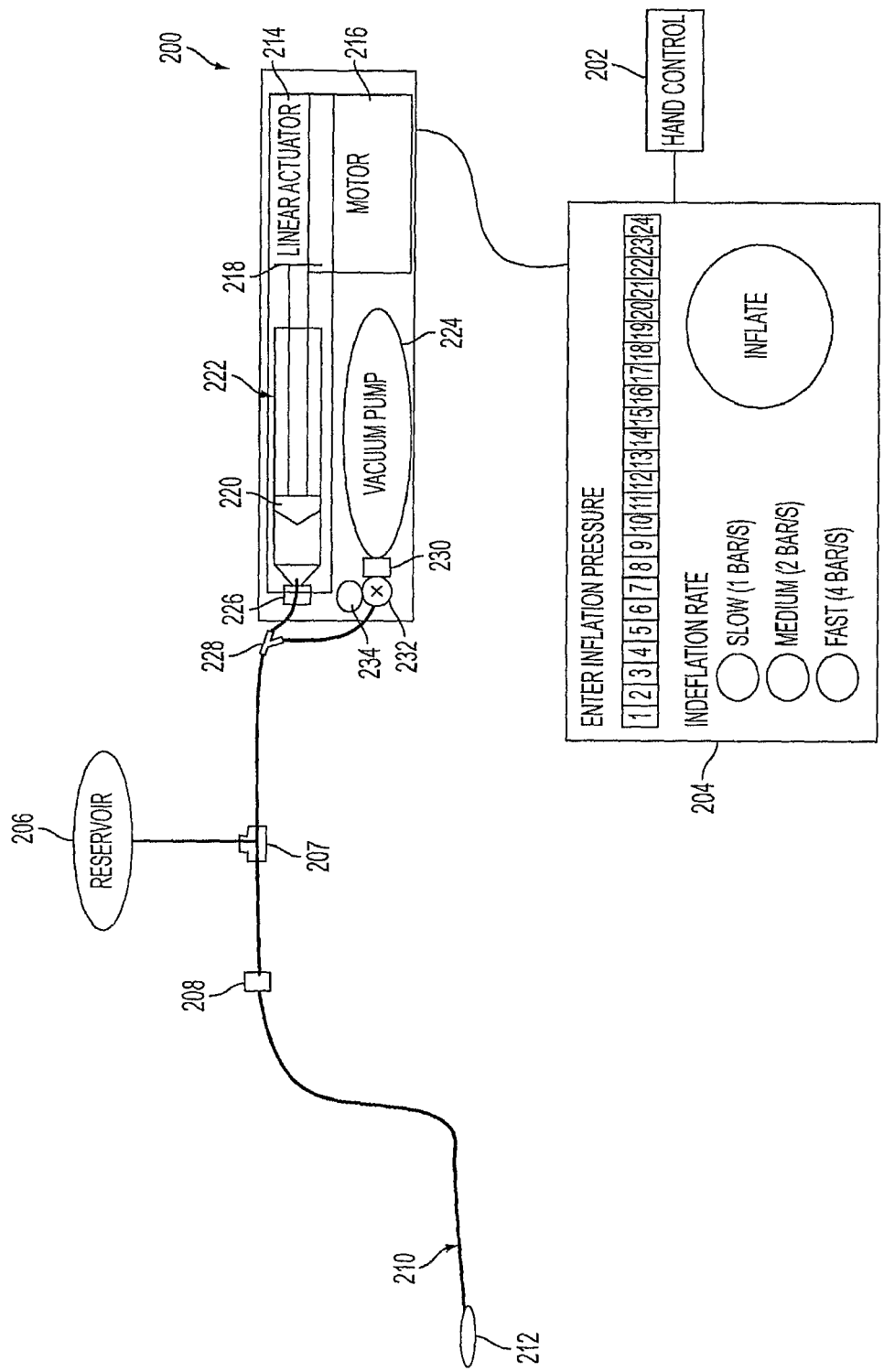
FIG. 11 is a block diagram of one embodiment of a balloon inflation device.

FIG. 11 is a block diagram of one embodiment of a powered balloon inflation device for use during a medical procedure, such as an angioplasty procedure. As is shown in FIG. 11, the balloon inflation device comprises a unit 200 that includes a syringe 222, a vacuum pump 224, a linear actuator 214, and a motor 216. The vacuum pump 224 is operatively coupled to the syringe 222. The unit 200 is coupled to balloon catheter 210 and also to a control panel 204. The control panel 204 is further coupled to a hand-control device 202. In one embodiment, the hand-control 202 device is not used. A user of the balloon inflation device may use the control panel 204 to control balloon preparation, as well as inflation and/or deflation of the balloon 212 coupled to the balloon catheter 210, as will be described in more detail below. The balloon 212 is located at a distal end of the catheter 210, according to one embodiment. This description generally refers to a balloon catheter that is coupled to a balloon, though the catheter that is actually used may be coupled to any form of such device, such as a cutting balloon or a stent-balloon. In one embodiment, the balloon inflation device is a stand-alone device, wherein a computerized system controls operation of the device. In one embodiment, the balloon inflation device is coupled to and controlled by an angiographic injection system, such as an embodiment of an injection system generally described above. The angiographic injection system may control the operation of the motor 216, linear actuator 214, and vacuum pump 224. In addition, the angiographic injection system may also control operation of the control panel 204 and receive signals from the hand-control device 202. In one embodiment, the control panel functionality may be merged into the functionality of the control panel of the angiographic injection system, such that a common control panel is used to control both devices.

In the embodiment shown in FIG. 11, the unit 200 comprises the syringe 222 and the vacuum pump 224. The syringe 222 may be used to inflate the balloon 212 (such as with a fluid medium of contrast or a contrast/saline mixture) and to deflate the balloon 212, and the vacuum pump 224 may be used to aspirate air from the balloon 212 during setup/purge. In one embodiment, these acts may occur during a series of distinct motorized operations of the device, such as through operation of the motor 216 and/or the pump 224. The syringe 222 includes a plunger 218 (which may also be referred to as a syringe ram), and also a wiper 220. The syringe ram 218 is driven by the linear actuator 214 (which is coupled to the motor 216) to draw fluid into or expel fluid from the syringe 222. The balloon inflation device is coupled to the balloon catheter 210 and to the balloon 212. One embodiment of such coupling is described below.

The output port of the syringe 222 is coupled to a tubing "Y" connector 228 via a bonded fitting 226. The tubing "Y" connector 228 is coupled to the balloon catheter 210 via a luer fitting 208, and is further coupled to the vacuum pump 224 via a rotating (2-way) stopcock 232, a three-way stopcock 207, and luer fitting 230. In one embodiment, the syringe 222, balloon catheter 210, balloon 212, bonded fitting 226, tubing for "Y" connector 228, luer fitting 208, luer fitting 230, stopcock 207, and rotating stopcock 232 are disposable components that may be discarded after each patient use. The syringe 222 is initially filled with fluid (such as contrast or a mixture of contrast and saline) by retracting the plunger 218 through movement of the linear actuator 214. This fluid is contained in a fluid reservoir 206. The fluid reservoir 206 is only operatively coupled to the tubing between the syringe 222 and the balloon catheter 210 when the syringe 222 is in the fill mode to fill liquid, according to one embodiment. In one embodiment, the three-way stopcock 207 is used when coupling the fluid reservoir 206 to the tubing, and is turned off to the balloon 212 in the balloon catheter 210 when the syringe 222 is drawing in fluid from the reservoir 206. In one embodiment, this stopcock 207 is a manual stopcock. In one embodiment, the stopcock 207 replaces the luer fitting 208 to the catheter 210. In one embodiment, the fluid reservoir 206 comprises a bowl or other form of container. In one embodiment, the fluid reservoir 206 comprises a syringe that is capable of containing fluid.

During inflation of the balloon 212, the linear actuator 214 causes the plunger 218 to move to expel the fluid from the syringe 222 and inject such fluid into the balloon catheter 210 and balloon 212. During deflation, the linear actuator 214 retracts the plunger 218 to aspirate fluid from the balloon catheter 210 and balloon 212 and draw such fluid back towards, or into, the syringe 222. In one embodiment, the stopcock 207 is turned off to the reservoir 206 during inflation and deflation operations.

As noted above, the vacuum pump 224 is used to aspirate air from the balloon catheter 210 and balloon 212 during setup/purge. The vacuum pump 224 is driven by the motor 216 in the unit 200. During the operation of air aspiration, the stopcock 207 is turned off to the reservoir 206, according to one embodiment. The rotating stopcock 232 is driven by a solenoid valve rotator 234, as shown in the embodiment of FIG. 11. The solenoid valve rotator 234 is used to couple the vacuum pump 224 with the tubing to evacuate air from the tubing or balloon 212 during setup/purge. However, the solenoid rotator 234 closes off the valve to cut off the vacuum line during inflation or deflation motorized operations. The linear actuator 214 and motor 216 may be used to drive balloon inflation and deflation. The unit 200 may need to apply sustained positive or negative pressure for prolonged periods. For example, positive pressure may need to be sustained for up to twenty minutes, and negative pressure may need to be sustained for up to multiple hours. In one embodiment, a locking mechanism on the actuator 214 can save motor time.

In one embodiment, the system shown in FIG. 11 includes a sensor (not shown) that is capable of measuring or calculating fluid pressure during an inflation or deflation cycle. In one embodiment, an in-line fluid pressure transducer is used to measure fluid pressure. In one embodiment, a force transducer or load cell is operatively coupled to the plunger 218 to calculate pressure. In one embodiment, motor current of the motor 216 is used to calculate pressure. In one embodiment, an air detector (not shown), such as an air-column detector, is used to detect the presence of air in the system, such as air bubbles or air columns. In one embodiment, this air sensor is operatively coupled to the output of the syringe 222.

Figure 12:
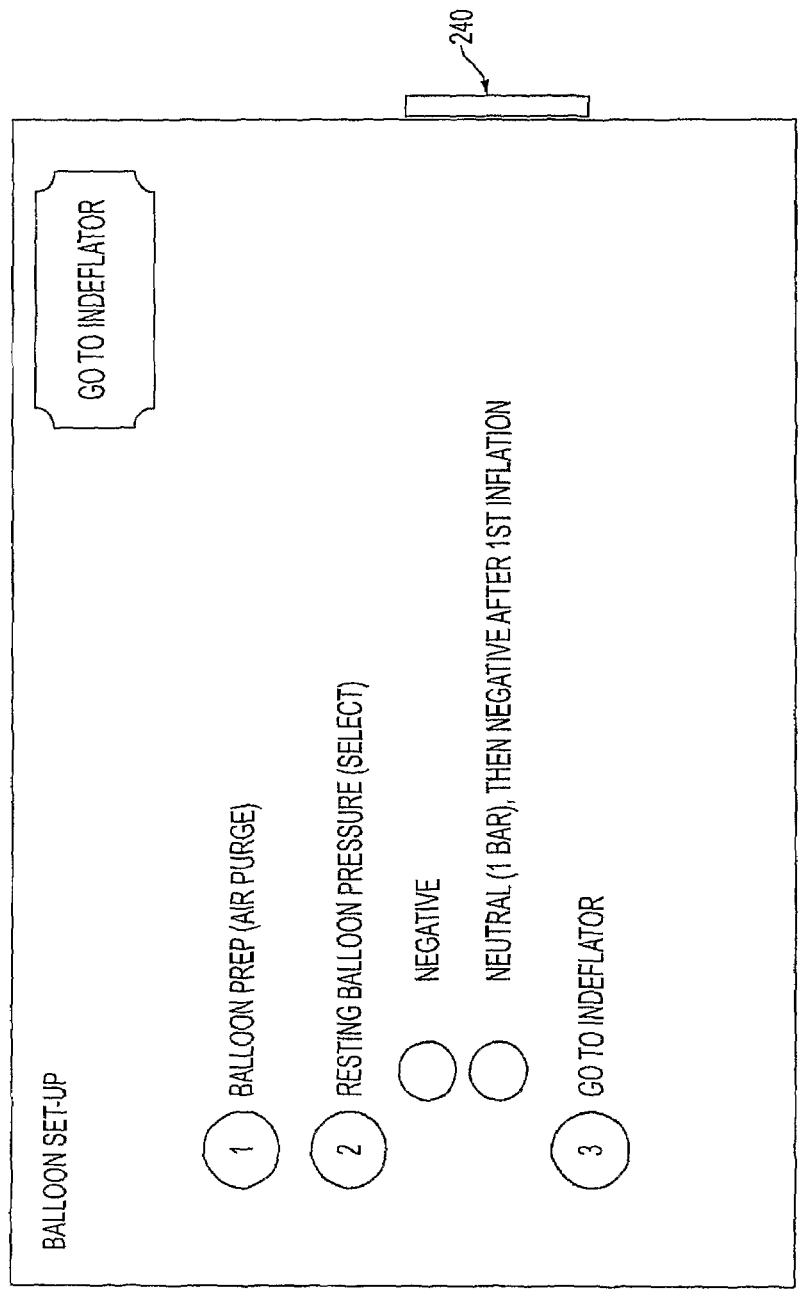
FIG. 12 through FIG. 14 are visual diagrams of information that may be displayed to a user of a balloon inflation device, according to one embodiment.
Figure 13:
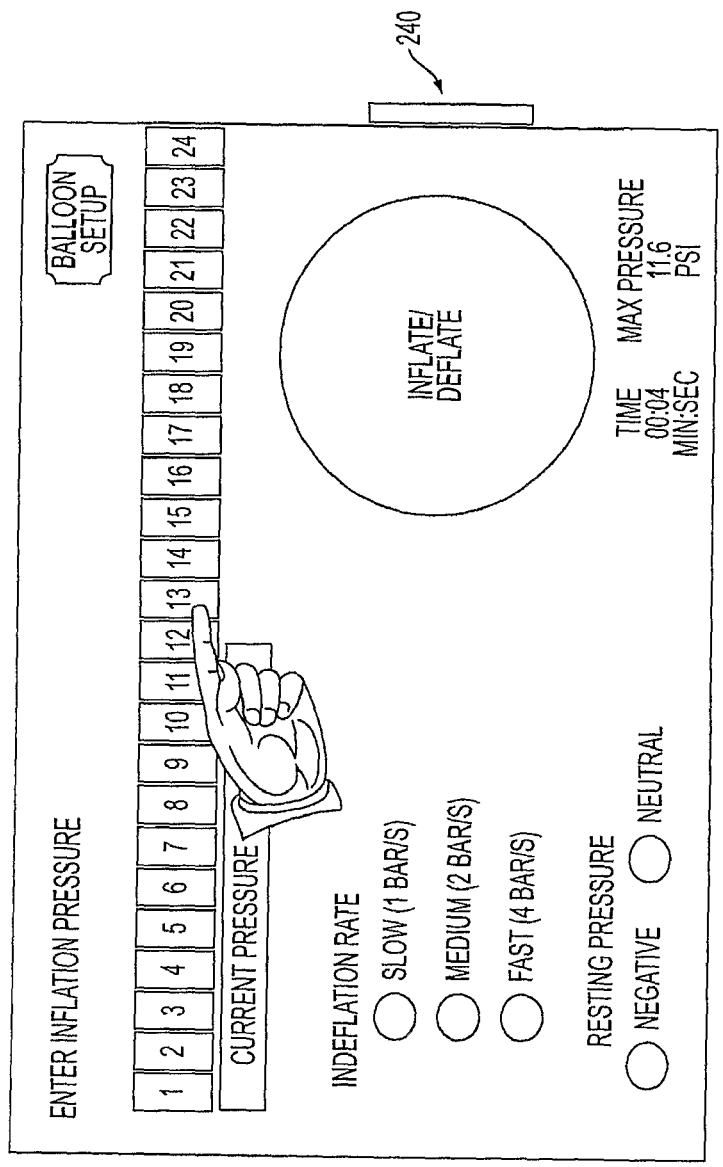
Figure 14:
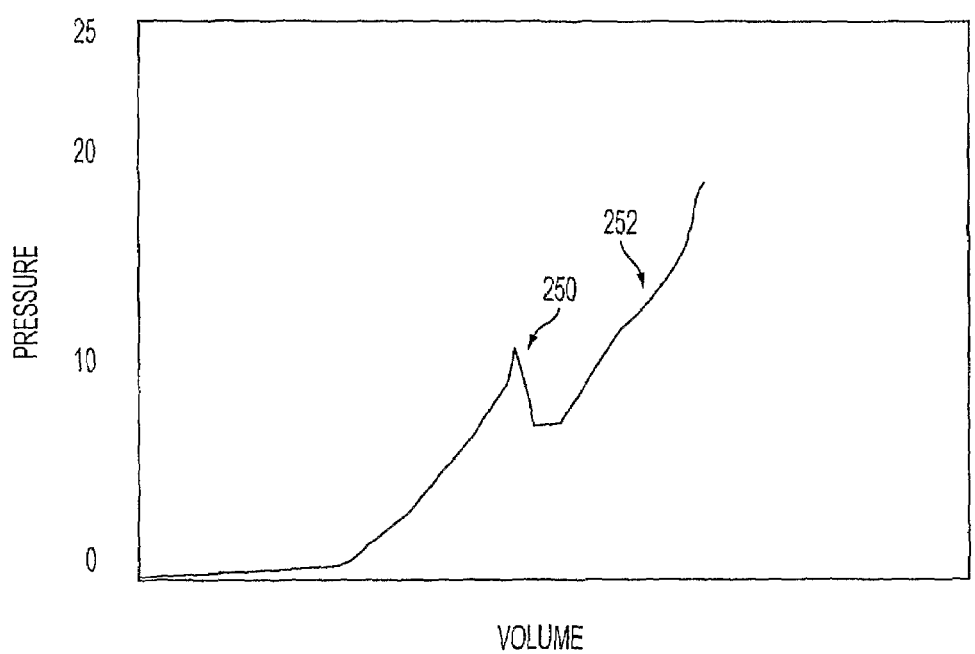

The control panel 204 is coupled to both the unit 200 and to the hand control 202, according to one embodiment. FIG. 12 through FIG. 14 show various examples of information that may be visually displayed by the control panel 204 to a user, which may include status information. The user may interact with the control panel 204 to provide information that may be used to control setup/purge, inflation, or deflation of the balloon catheter 210 and balloon 212. The user may also use the hand control 202 to control inflation or deflation of the balloon 212. In one embodiment, the hand control 202 is a variable-rate hand control that comprises a controller, such as a button, knob, or other actuating mechanism. The user may use the controller to control inflation or deflation. The rate of inflation or deflation will be based upon the amount of pressure applied by the user's hand or finger(s) to the controller. For example, the user may press gently on the controller to achieve a slow rate of inflation (or deflation), but may press much harder to achieve more rapid inflation (or deflation). In one embodiment, the hand control 202 is an electronic hand-control device. In one embodiment, the hand control 202 is a pneumatic hand-control device.

FIG. 12 is an example of a visual diagram of information that may be displayed to a user of the control panel 204 shown in FIG. 11. The user may, for example, interact with the control panel 204 to setup the balloon catheter 210 and balloon 212. In one embodiment, the control panel 204 includes a touch-screen. Once the balloon catheter 210 and associated tubing are connected to the unit 200, the user may begin the set up/purge process by, for example, pressing the "Balloon Prep (air purge)" button that is shown in FIG. 12 (on the control panel 204). Pressing this button provides a single user input command by the user to draw in an amount of fluid from the reservoir 206 into the syringe 222, and removing an amount of air from the balloon 212 and/or catheter 210, according to one embodiment. The linear actuator 214 drives the plunger 218 of the syringe 222 to fill in an amount of fluid from the reservoir 206 to the syringe 222 during one motorized operation. The stopcock 207 then turns off the connection to the reservoir 206. The solenoid valve 234 is then turned on to the vacuum pump line, and the vacuum pump 224 is turned on to evacuate air from the balloon 212 during another motorized operation. Once air has been evacuated, the solenoid is turned off to the pump.

The user may then select the resting pressure state by, for example, pressing the "Resting balloon pressure" button that is shown in FIG. 12. According to the example shown, the user may either select "Negative" or "Neutral". When using stents, the user will usually select "Neutral" and then negative after the first inflation. When using balloons only, the user will typically select "Negative". Once the user has selected a resting pressure, the user may then press the "Go to Indeflator" button to begin inflation. ("Indeflator" refers to an inflator/deflator.) Inflation and deflation actions may then occur during subsequent motorized operations, according to one embodiment.

FIG. 13 is a visual diagram of an exemplary screen that may be displayed to the user after having pressed the "Go to Indeflator" button, as described above. The user is able to select a desired inflation pressure and also a desired rate of inflation/deflation. The example of FIG. 13 shows three indeflation (inflation/deflation) rates: slow, medium, and fast. Various other preconfigured rates may be used. In addition, the user may be allowed to select a specific rate. The user may press, for example, the "Inflate/Deflate" button to activate inflation or deflation cycles. Once an inflation begins, a timer is started and displayed to the user. The maximum pressure is also displayed. The timer times a full inflation period, according to one embodiment. During inflation, a pressure gauge is displayed as "current pressure".

During inflation, the user can change the inflation pressure at any time by pressing, for example, a new target on the screen. In one embodiment, there are no confirmations of changes in inflation pressure, as timing may be quite important. In addition, the user can change the inflation (or deflation) rate at any time. When inflation is completed, the user can press the "Inflate/Deflate" button to begin deflation at the selected rate. There is also, in one embodiment, an "emergency" deflate button, switch, lever, or other mechanism 240 to override all other controls and trigger a rapid deflate operation of the balloon 212. All pressure and timing data can be output to a printer or other recording device, and may also be saved on a storage medium that is coupled to the control panel.

The user may alter the resting pressure of the balloon catheter 210 and balloon 212, for example, by selecting either "Negative" or "Neutral" on the exemplary screen that is shown in FIG. 13. In addition, if the user wants to prep, or set up, a new balloon catheter that is to be used with the inflation device, the user may press the "Balloon Setup" button, which will cause the control panel 204 to again display the screen that is shown in FIG. 12.

In one exemplary embodiment, the control panel 204 may also display to the user a pressure-volume curve during an inflation of the balloon catheter 210. One such example is shown in FIG. 14. This graph shows pressure in the balloon as a function of the volume of fluid (e.g., contrast or contrast/saline mixture) that has been injected into the balloon catheter during inflation. When the balloon is inflated, the balloon often hugs the wall of a stenotic vessel. As fluid is injected into the balloon, the pressure usually rises in a linear fashion. When a lesion "cracks", the pressure in the balloon may momentarily fall, as is shown at area 250 in FIG. 14. Additional volume injection results in a marked increase in balloon pressure when maximal inflation has been achieved, and when the balloon is apposed to the vessel wall, as shown in area 252 of FIG. 14. By viewing the pressure-volume curve data that is shown in FIG. 14, the user may be able to determine when the lesion has "cracked", and may then take appropriate action (as described in some detail previously).

Figure 15A:
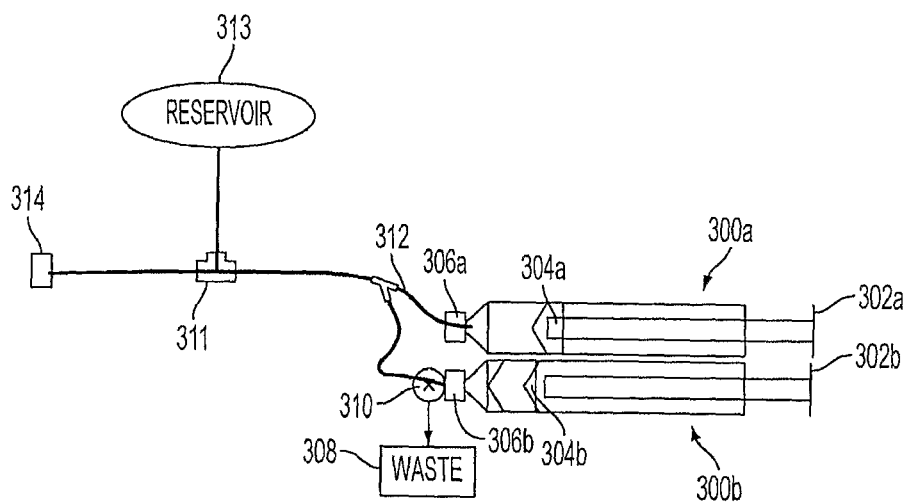
FIG. 15A through FIG. 15C are block diagrams of embodiments of various components of a balloon inflation device.
Figure 15B:
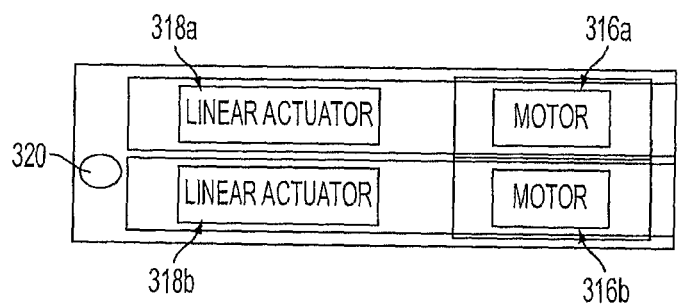
Figure 15C:
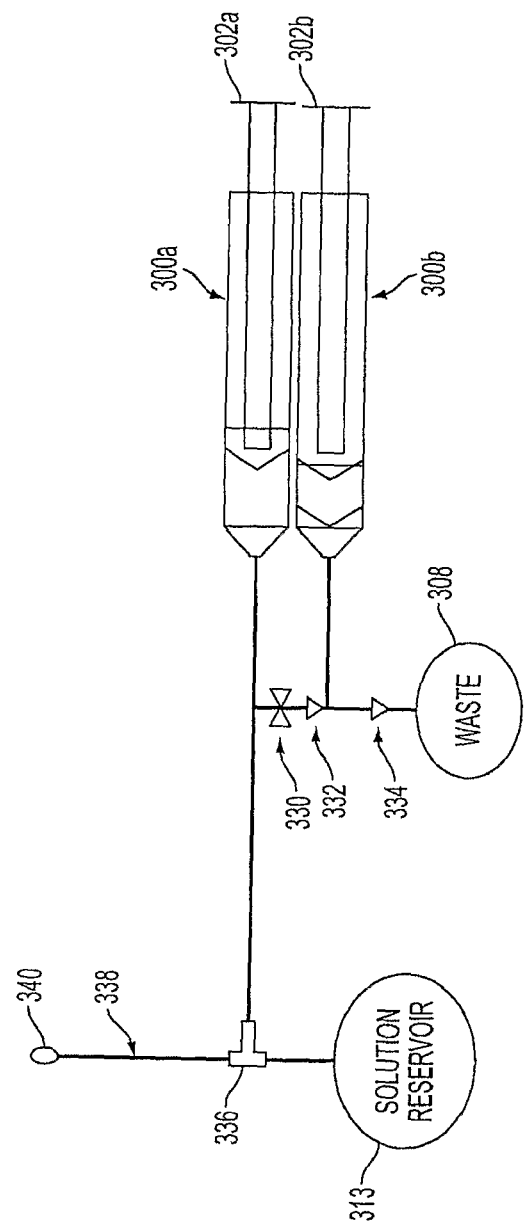

FIG. 15A through FIG. 15C are block diagrams of embodiments of various components of a balloon inflation device. In these embodiments, the balloon inflation device comprises a second syringe rather than a vacuum pump. For example, FIG. 15A shows a first syringe 300a and a second syringe 300b. The syringe 300a is operatively coupled to the syringe 300b. Each syringe attaches to a distinct syringe ram, or plunger. For example, the syringe 300a includes a plunger 302a, and the syringe 300b includes a plunger 302b. The first syringe 300a is coupled with the first assembly shown in FIG. 15B. The first assembly comprises a first linear actuator 318a that is driven by a first motor 316a. The linear actuator 318a actuates a first syringe ram that drives the plunger 302a of the syringe 300a. The second syringe 300b is coupled with the second assembly, which comprises a second linear actuator 318b that is driven by a second motor 316b. The linear actuator 318b actuates a second ram that drives the plunger 302b of the syringe 300b. In one embodiment, the acts of drawing fluid in from the reservoir 313, removing air from the line, inflation, and deflation are provided by distinct motorized operations of the device, such as by distinct operation of the motors 316a and/or 316b over various operating cycles. In one embodiment, the inflation device includes a sensor capable of measuring or calculating fluid pressure, such as described above. The inflation device may also include an air sensor, control panel, or hand control, such as is described above.

In the embodiment shown in FIG. 15A, each syringe 300a and 300b is, for example, the same size, preferably a 12 cc syringe. The plunger 302a includes a wiper 304a on one end. Similarly, the plunger 302b includes a wiper 304b on one end. A fitting 306a is coupled to the output of the syringe 300a, and a fitting 306b is coupled to the output of the syringe 300b. The first syringe 300a is used to inflate (by injecting fluid into) the balloon catheter (not shown) through movement of the plunger 302a, as well as to deflate (by evacuating fluid from) the balloon catheter. The balloon catheter is coupled to the device via a connector 314. The first syringe 300a is initially filled with an amount of fluid (such as contrast or a mixture of contrast and saline) from a reservoir 313 through line 312 that is used for injecting into the balloon catheter during inflation. In one embodiment, a three-way stopcock 311 is used. During a fill operation, the stopcock is closed to the line to the connector 314, according to one embodiment. The second syringe 300b is used in place of the vacuum pump (described previously) to aspirate air from the balloon catheter (for example, during setup) and also to evacuate fluid from the line. In one embodiment, the stopcock 311 is closed to the reservoir 313 during an air removal operation. As shown in FIG. 15A, the second syringe 300b is coupled to a rotating, 3-way stopcock 310. The 3-way stopcock 310 is used so that the second syringe 300b can expel waste (e.g., fluid) into a waste line 308. A solenoid valve rotator 320 shown in FIG. 15B controls the 3-way stopcock 310. The second syringe 300b may use two or more cycles to aspirate fluid from the line or balloon catheter and expel the fluid into the waste line 308. During each cycle, the solenoid valve rotator 320 closes the stopcock 310 to waste 308, such that the second syringe 300b can aspirate fluid from the line or catheter. The linear actuator 318b is used to retract the plunger 302b in the second syringe 300b during aspiration. The solenoid valve rotator 320 then closes the stopcock 310 to the tubing, such that the second syringe 300b can expel the fluid to the waste line 308. In one embodiment, the waste line 308 comprises a waste bag or bowl.

FIG. 15C shows another embodiment of a dual-syringe implementation, wherein a pinch valve 330, one-way valves 332 and 334, and a 3-way stopcock 336 are used. The 3-way stopcock 336 may be controlled again by a solenoid valve rotator, according to one embodiment. The pinch valve 330 may be actuated by a pneumatic, electronic, solenoid, or other controlling device that is coupled to the unit. In this embodiment, the first syringe 300a is used to inflate or deflate the balloon catheter 338 and balloon 340. The second syringe 300b may be used during setup to aspirate fluid from the line and expel to the waste line 308.

In one embodiment, the setup of the balloon inflation device operates as follows. Initially the 3-way stopcock 336 is closed to the balloon catheter 338, such that the first syringe 300a is coupled to the solution reservoir 313 (which may contain, for example, a liquid mixture of contrast and saline in a selected concentration). The plunger 302a of the first syringe 300a is retracted through movement of the first linear actuator 318a to draw fluid from the solution reservoir 313 into the first syringe 300a during a first motorized operation of the motor 316a. The 3-way stopcock 336 is then closed to the solution reservoir 313, such that the first syringe 300a becomes coupled with the balloon catheter 338. The pinch valve 330 is opened, such that the second syringe 300b is also coupled with the balloon catheter 338. The plunger 302b of the second syringe 300b is retracted through movement of the second linear actuator 318b to aspirate fluid (including any liquid or air) from the balloon catheter 338 and balloon 340 and the fluid line coupled to both the first and second syringes 300a and 300b during another motorized operation of the motor 316b. In addition, this movement of the second linear actuator 318b may also draw some fluid out of the first syringe 300a. The first syringe 300a may be angled so that not all of its fluid is extracted.

The pinch valve 330 is then closed. The plunger 302b of the second syringe 300b is moved to expel fluid from the second syringe 300b and the fluid line into the waste container 308 during another motorized operation of the motor 316b. The closed pinch valve 330 restricts fluid flow back towards the first syringe 300a or balloon catheter 338. In addition, the one-way valves 332 and 334 also restrict fluid flow to one direction (towards the second syringe 300b and waste container 308). These steps may be repeated one or more times to ensure that air is aspirated from the balloon catheter 338/ balloon 340 and from the first syringe 300a. The pinch valve 330 can then be closed, and the balloon catheter 338 and balloon 340 are ready for inflation by the first syringe 300a during a motorized operation of the motor 316a. The first syringe 300a is also used to deflate the balloon 340 when the first linear actuator 318a retracts the plunger 302a of the first syringe 300a during a motorized operation of the motor 316a. During deflation, the pinch valve 330 is also in the closed position. In one embodiment, each of the motorized operations of the motor 316a and/or 316b are different operations that occur during different operating cycles.

Figure 16A:
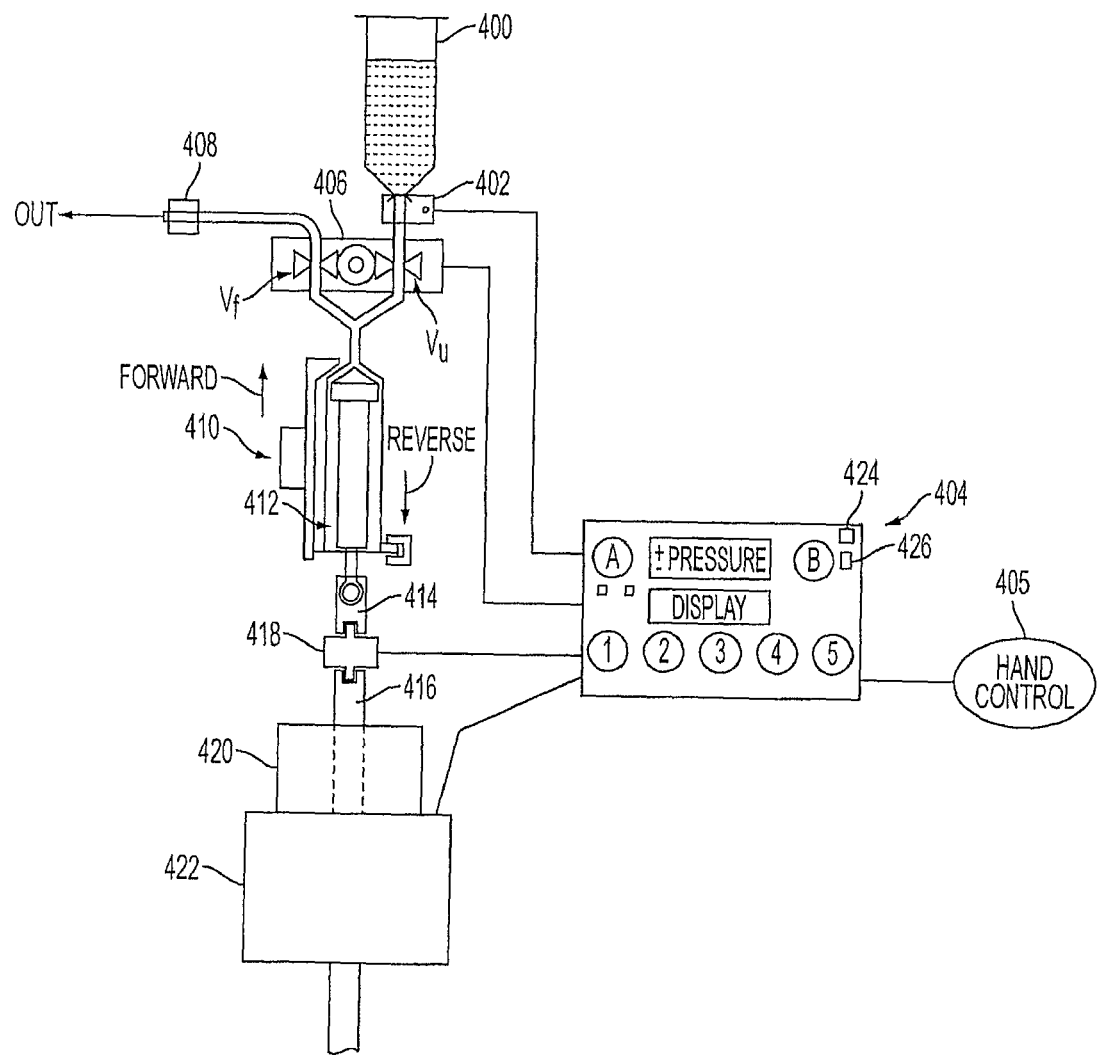
FIG. 16A is a block diagram of another embodiment of a balloon inflation device.

FIG. 16A is a block diagram of another embodiment of a balloon inflation device. This embodiment utilizes a single syringe 412. The syringe 412 is mounted to a housing 410 for purposes of stability. The syringe 412 has a fluid port that is coupled to multiple tubing channels via a Y-connector. A first tubing channel is coupled to a solution reservoir 400, and a second tubing channel may be coupled to the line to the balloon catheter (not shown) via connector 408. In one embodiment, the solution reservoir 400 comprises a bowl or other form of container. In one embodiment, the solution reservoir 400 comprises a syringe that is capable of containing fluid.

Two pinch valves (labeled $V_f$ and $V_u$ in FIG. 16A) are used to open and close fluid flow through the tubing channels. These pinch valves may be controlled by a pneumatic, electronic, solenoid, or other control mechanism. An air-column-detect (ACD) sensor and ball valve are included in a mechanism 402 that is coupled to the first tubing channel. In one embodiment, the ACD sensor is an optical sensor that is used to detect air bubbles or air columns in the line. The ACD sensor may also comprise an ultrasonic sensor, in another embodiment. The ball valve allows liquid to flow from the solution reservoir 400 into the syringe 412, and further allows air to flow from the syringe 412 and tubing channel back into the solution reservoir 400. However, the ball valve restricts flow of liquid from the syringe 412 and tubing channel into the reservoir 400, and, in combination with the ACD sensor, restricts flow of air into the channel (downstream of the $V_u$ pinch valve) and into the syringe 412 or, ultimately, to the balloon catheter.

The plunger is coupled to a rod 414 using a ball-socket coupling, according to the example shown in FIG. 16A. Other forms of coupling may be used. A rod 416 is coupled to a linear actuator 420, which is capable of driving the rod 414 and 416 forwards and backwards (up and down in FIG. 16A). The actuator 420 is driven by a motor 422. The rod 414 and 416 are coupled, as shown, to a force sensor 418. The force sensor 418 is positioned such that it is capable of sensing forces applies by the rod 416 when moving in the forward (up) direction, and capable of sensing forces applied by the rod 414 when moving in the backward (down) direction. The signals generated by the force sensor 418 can be used to calculate a vacuum pressure (when the rods 414 and 416 move in the backward direction to pull back the plunger and draw fluid into the syringe 412), and may also be used to calculate inflation pressure (when the rods 414 and 416 move in the forward direction to cause the plunger to expel fluid from the syringe 412).

A unit 404 is used to control and monitor the motor/actuator 420 and 422 and the pinch valve assembly. This unit 404 is coupled to a control panel. Signals from the optical sensor (in mechanism 402) and force sensor 418 are provided to the unit 404 for processing. As shown in FIG. 16A, the control panel includes a power indicator 424 and a status indicator 426. The status indicator 426 may include one or more lights to indicate various different statuses of the device. In one embodiment, these lights may be of different color. The control panel also includes various buttons and/or activators. It may include a touch-screen. Activator A allows a user to select positive and negative pressure limits. The user can select a negative pressure limit for vacuum or deflation, and can select a positive pressure limit for inflation. Activator A may also allow a user to select inflation or deflation rates of pressure change. Activator B comprises an emergency deflate option to provide rapid deflation (wherein the motor provides full current to cause retraction of the plunger).

In one embodiment, the inflation device provides various motorized operations through operation of the motor 422. For example, the acts of filling the syringe 412 with fluid from the reservoir 400, removing air from the tubing, inflation, and deflation occur during different motorized operations of the motor 422 during different operating cycles.

The user may activate "Button 1" to fill the syringe with liquid from the solution reservoir 400. The user may activate "Button 2" to pull a vacuum in the tubing channels and/or balloon catheter. The user may activate "Button 3" to purge and inflate the balloon catheter. The user may activate "Button 4" to deflate the balloon catheter. The plunger is retracted (down, in the reverse direction as shown in FIG. 16A) when Buttons 1, 2, or 4 are depressed. The plunger is moved up (in the forward direction), in the opposite direction, when Button 3 is depressed, in one embodiment.

Figure 16B:
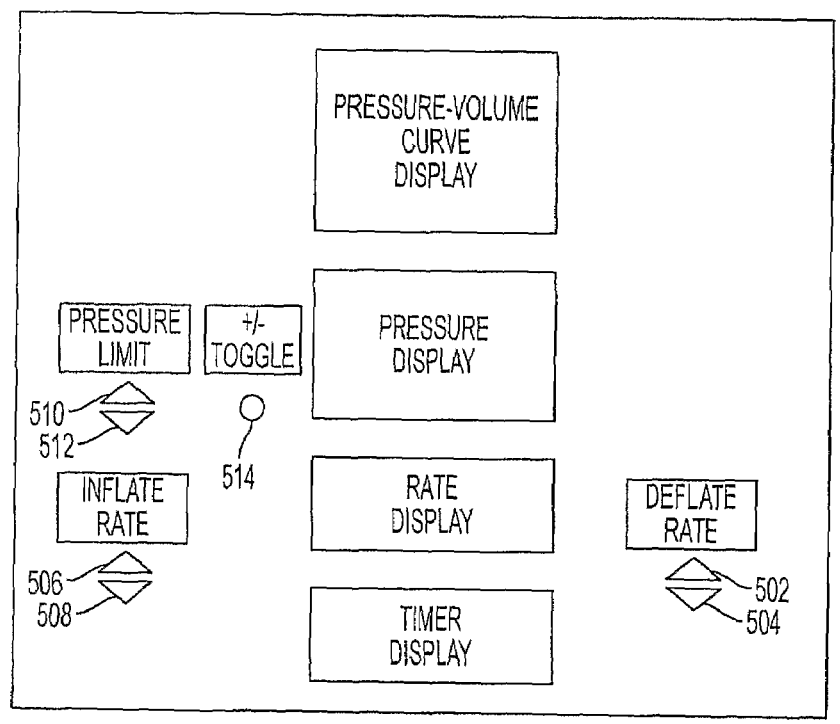
FIG. 16B is a visual diagram of additional components that may be displayed on the control panel of FIG. 16A.

Various display information may also be provided on the control panel in the unit 404. For example, the pressure, rate of pressure change, and inflation time may all be displayed. FIG. 16B shows an example of various components that may be displayed on the control panel. Various other information, such as information described above, may be displayed on the control panel as well. In one embodiment, a hand-control device 405, such as the hand-control device shown in FIG. 11 and described above, may also be coupled to the control panel shown in FIG. 16A. In one embodiment, the balloon inflation device is a stand-alone device, wherein a computerized system controls operation of the device. In one embodiment, the balloon inflation device is coupled to and controlled by an angiographic injection system, such as is generally described above. The angiographic injection system may control the operation of the motor 422, linear actuator 420, pinch valves, and syringe 412. In addition, the angiographic injection system may also control operation of the control panel and receive signals from the ACD sensor (in mechanism 402) and force sensor 418. In one embodiment, the control panel functionality may be merged into the functionality of the control panel of the angiographic injection system.

In one embodiment, the hand-control device 405 is coupled to the control panel shown in FIG. 16A. This hand-control device 405 may be similar to the one shown in (and described above in reference to) FIG. 11. The control panel may also include user controls (not shown) that allow a user to control the manual opening and closing of the pinch valves $V_f$ and $V_u$. The user may utilize these user controls when inserting tubing into or removing tubing from the device through the pinch-valve assemblies. The user may also utilize these controls to test the inflation device and override the automatic control of the pinch valves by the device during operation, according to one embodiment. The balloon inflation device is capable of automatically controlling operation of the pinch valves during setup (fill, vacuum), inflation, and deflation, but the user may also manually control the pinch valves during these operations, as well, for testing purposes.

FIG. 16B is a visual diagram of additional components that may be displayed on the control panel of FIG. 16A. The pressure-volume curve, as described previously may be displayed. In addition, the pressure, rate of pressure display, and inflation timer may also be displayed. As shown, the user may adjust the pressure limit using, for example, arrow keys 510 and 512. The user may toggle between positive and negative pressure by using a toggle button 514, or may select between positive and negative pressure in an alternate way, before adjusting the pressure limit using the arrow keys 510 and 512. The pressure display may show the selected pressure limit(s), and may also show the calculated in-line pressure for the balloon catheter during inflation/deflation. The user may also adjust the inflation or deflation rates by using, for example, the arrow keys 506 and 508 for inflation, and arrow keys 502 and 504 for deflation. The rate display may display the selected inflation/deflation rates, and, after selected, may then also show the in-line pressure for the balloon catheter during inflation/deflation. In one embodiment, the control panel provides a touch screen for activation by the user.

Figure 16C:
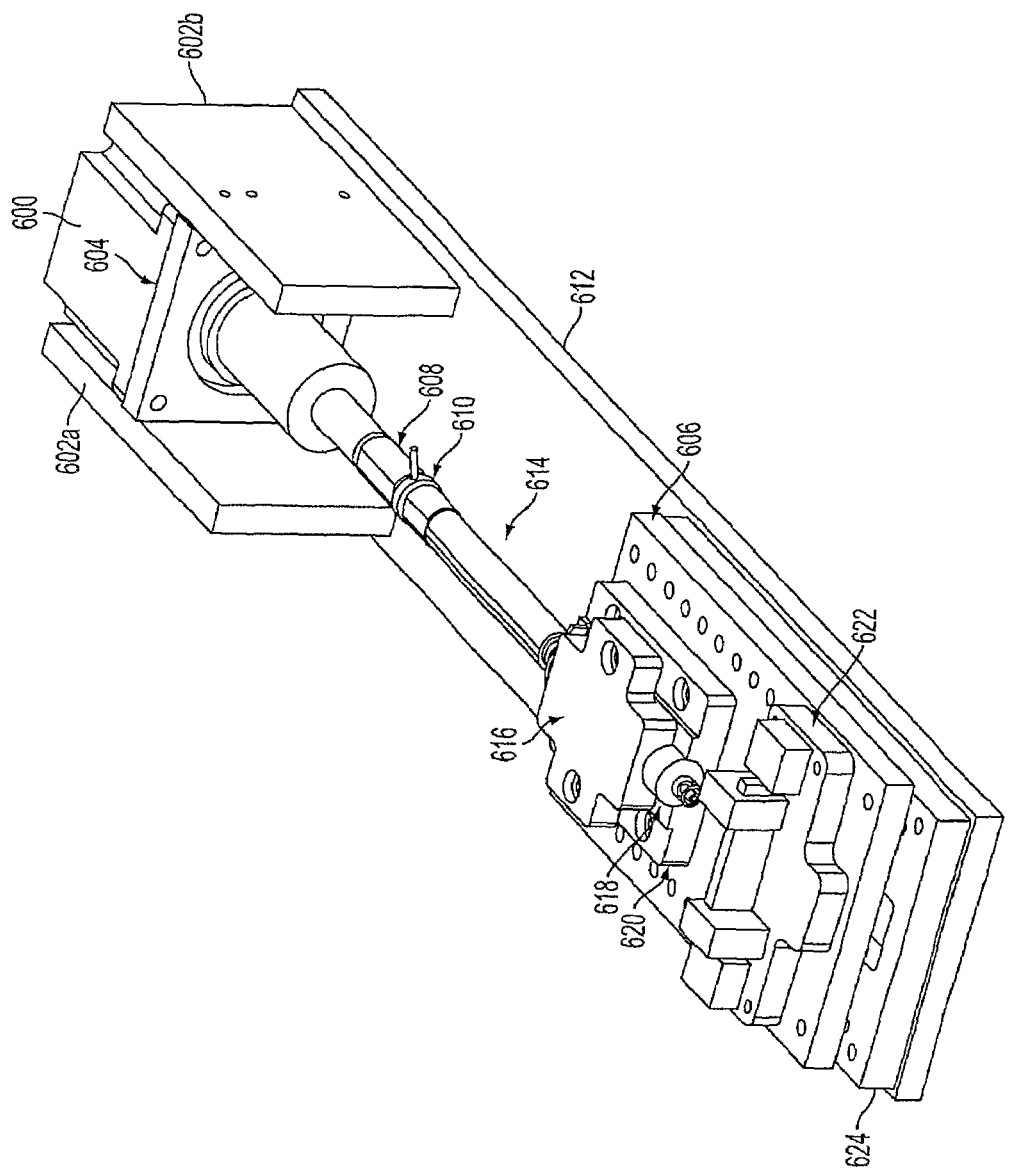
FIG. 16C is a block diagram of an alternate embodiment of a portion of a balloon inflation device.

FIG. 16C is a block diagram of an alternate embodiment of a portion of a balloon inflation device. This embodiment is similar to the embodiment shown in FIG. 16A. Although not shown in FIG. 16C, the balloon inflation device shown in this figure may be coupled to a medical fluid reservoir, a patient line, and a control panel in one embodiment, similar to the device shown in FIG. 16A.

In FIG. 16C, the device includes a linear actuator 600, a motor face plate 604, and motor side plates 602a and 602b. The linear actuator 600 is driven by a motor. The motor face plate is located between and couples the motor side plates 602a and 602b. The device further includes a motor/load cell connection 608, a load cell 610, a base plate 612, a syringe plunger 614, a syringe cover 616, a syringe pinch valve plate 606, a syringe 618, a pinch valve 622, a syringe nest 620, and a syringe rail 624. The base plate 612 supports a bottom side of the device. A load cell 610 is used to detect and measure force that is applied by the linear actuator 600 to the syringe plunger 614 through the connection 608, according to one embodiment. The syringe plunger 614 is coupled to the syringe 618, which can include medical fluid that is drawn in from a fluid reservoir and then injected into a patient. The syringe cover 616 is used to cover and protect the syringe on a top side, and the syringe nest 620 is also used to protect and hold the syringe on a bottom side. The pinch valve plate 606 supports both the syringe nest 620 and the pinch valve 622, and it rests upon the syringe rail 624. Similar to the embodiment shown in FIG. 16A, the inflation device of FIG. 16C includes a pinch valve 622 that is capable of controlling opening and closing of tubing components leading to and away from the syringe 618. The pinch valve 622 can open or close tubing leading to the syringe 618 from a fluid reservoir (shown in FIG. 16A), and can also open or close tubing leading from the syringe 618 to a patient line. The pinch valve 622 can be operated and controlled by a control unit, such as the unit 404 shown in FIG. 16A.

Figure 17A:
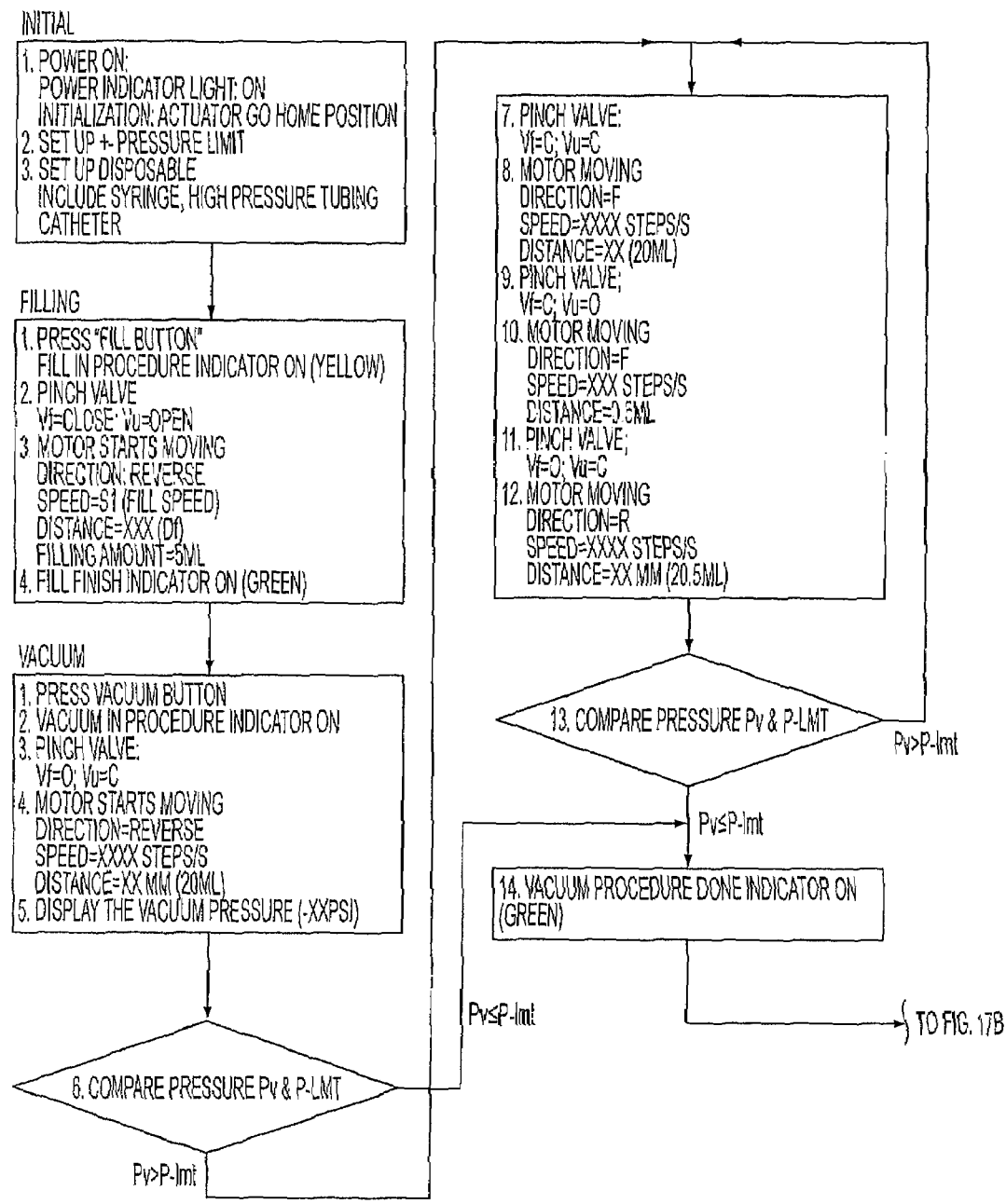
FIG. 17A and FIG. 17B are flow diagrams of various methods that may be performed by the balloon inflation device shown in FIG. 16A, according to one embodiment.
Figure 17B:
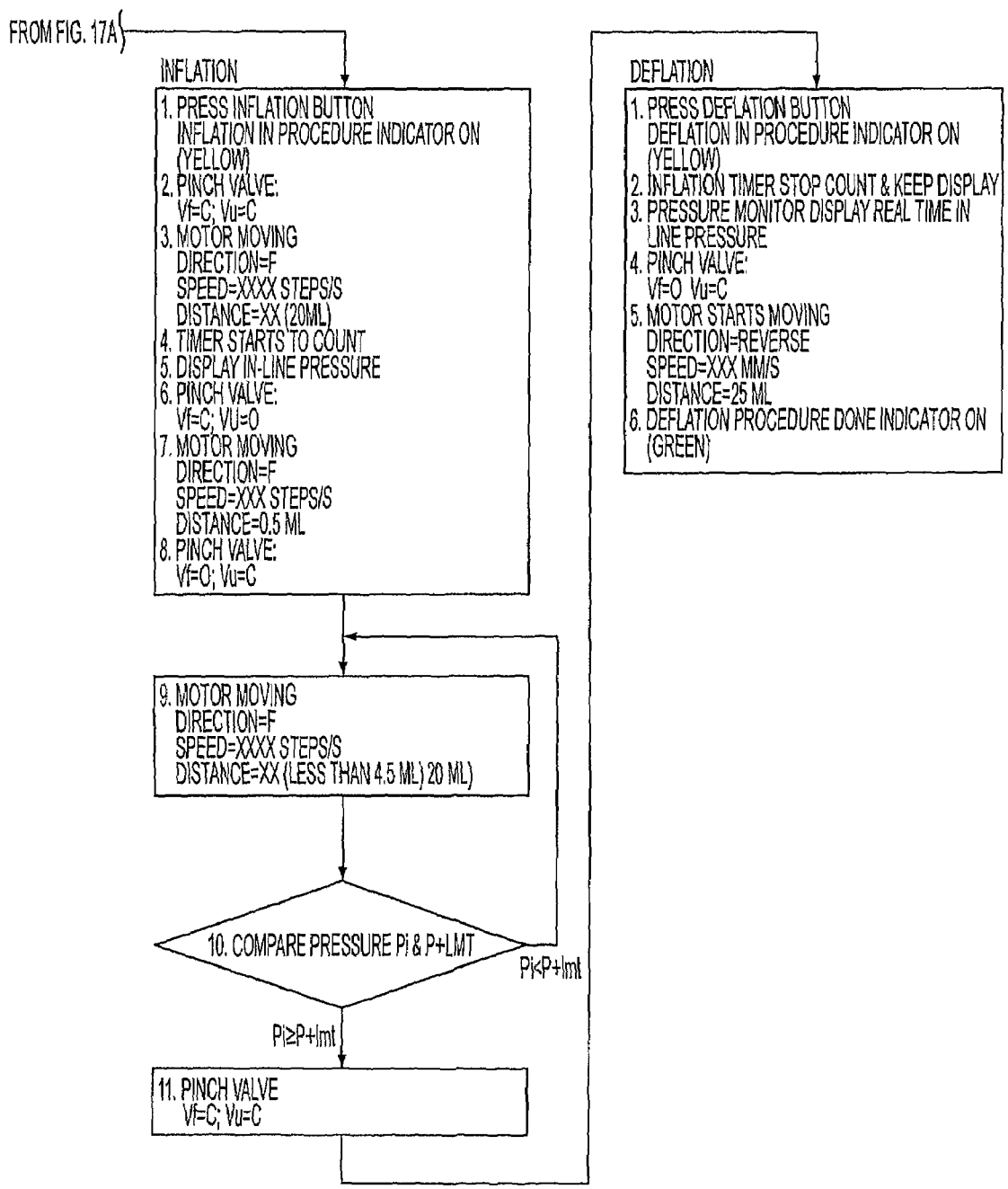

FIG. 17A and FIG. 17B are flow diagrams of various exemplary methods that may be performed by the balloon inflation device shown in FIG. 16A, according to one embodiment. The diagrams show methods for initialization, filling, drawing a vacuum, inflation, and deflation. Referring first to FIG. 17A, an initialization method is first shown. When the power to the inflation device is turned on, the power indicator 424 provides a power indicator light that turns on. The status indicator 426 may also provide status information for display to the user. The actuator 420 goes to a "home" position, which, in one embodiment, causes the plunger to move to the forward position (or up, as shown in FIG. 16A). The user may use the control panel to select the positive and negative pressure limits, and may also set up the disposables (including the syringe and high-pressure tubing and balloon catheter) by connecting to the unit.

For fill operations, the user may press the "Fill" button, which is "Button 1" as shown in FIG. 16A. The status indicator 426 may provide a fill indicator light (yellow) that turns on during fill operations. (In one embodiment, green and yellow indicator lights may be provided on the control panel for each operation, such as a fill, vacuum, inflation, or deflation operation. Display of a yellow light indicates that the operation is currently in process. Display of a green light indicates that the operation has completed.) The $V_f$ pinch valve is closed, to close off fluid communication with the balloon catheter, while the $V_u$ pinch valve is opened, to allow fluid communication between the syringe 412 and the solution reservoir 400. The motor 422 then causes the actuator 420 to move the plunger in the reverse direction, as shown in FIG. 16A, with a determined speed and at a certain distance. The fill speed and distance (# of steps if using a stepper motor) may be preconfigured on the balloon inflation device. In the example of FIG. 17A, the syringe is filled with 5 ml of fluid. The status indicator 426 provides an updated status when the fill operation is complete, such as by displaying a green light.

The balloon inflation device also is capable of automatically pulling a vacuum in the fluid line and balloon catheter. FIG. 17A shows various components of this procedure. The user can initiate the procedure by pressing the "Vacuum" button, which is "Button 2" as shown in FIG. 16A. The status indicator 426 provides a status indicating that the process of pulling a vacuum has been initiated. The $V_f$ pinch valve is opened, such that a vacuum can be drawn in the fluid line coupled to the balloon catheter. The $V_u$ pinch valve is closed. The plunger again moves in the reverse direction at a determined speed and for a determined distance. The vacuum pressure can be displayed on the control panel.

The vacuum pressure (Pv) is then compared to the negative pressure limit (P-lmt) that was previously set by the user. If the vacuum pressure is less than or equal to the negative pressure limit, then the vacuum procedure is completed, and the status indicator 426 on the control panel can indicate as such by showing a green light. If, however, the vacuum pressure is greater than the negative pressure limit, the balloon inflation device needs to try again to pull more vacuum. An iterative process is used until the vacuum pressure is loss than or equal to the negative pressure limit. This iterative process comprises actions 7 through 13, as shown in FIG. 17A. Both pinch valves $V_f$ and $V_u$ are closed. The motor 422 then moves to cause the plunger to move in the forward direction with a determined speed and for a determined distance. Then, the pinch valve $V_u$ is opened, such that there is fluid communication between the syringe 412 and the solution reservoir 400. The motor 422 then moves to cause the plunger to move in the forward direction with a determined speed and for a determined distance to push fluid back towards the solution reservoir 400 (and possibly pushing any air into the solution reservoir 400). At this point, the $V_u$ valve is closed and the $V_f$ valve is opened, such that the syringe 412 is coupled with the fluid line to the balloon catheter. The motor then moves to cause the plunger to move in the reverse direction with a determined speed and for a determined distance to pull vacuum. The vacuum pressure (Pv) is again compared to the negative pressure limit (P-lmt).

Once the procedure for obtaining vacuum has been completed, the inflation device is ready for inflating the balloon catheter. The inflation process is shown in FIG. 17B. To begin an inflation, the user presses the "Inflation" button, which is "Button 3" as shown in FIG. 16A. The status indicator 426 provides an indicator light (yellow) to indicate that an inflation procedure has begun. Both pinch valves $V_f$ and $V_u$ are closed. The motor 422 then moves to cause the plunger to move in the forward direction at a determined speed and for a determined distance, and the inflation timer begins counting. The in-line pressure can be displayed on the control panel. The $V_u$ valve is temporarily opened, and the plunger then moves in the forward direction to, for example, fill the line with a small amount of fluid. The $V_u$ valve is then closed and the $V_f$ valve is opened to couple the syringe 412 with the balloon catheter.

The motor then moves to cause the plunger to move in the forward direction at a determined speed for a determined distance to inject fluid into the balloon catheter for inflation. The inflation device is capable of calculating, or keeping track of, how much fluid remains in the syringe 412, according to one embodiment, for inflation purposes.

The inflation device then compares the inflation pressure Pi (which may also be displayed on the control panel) to the positive pressure limit (+Plmt) that was previously set by the user. If the pressure is greater than or equal to the limit, then both valves $V_f$ and $V_u$ are closed. If the pressure is less than the limit, then the plunger continues moving forward in incremental amounts (iteratively, as shown in FIG. 17B) until the pressure has equaled or exceeded the limit.

To begin the deflation process, which is also shown in FIG. 17B, the user presses the "Deflation" button, which is "Button 4" as shown in FIG. 16A. An indicator light may be displayed to indicate that the deflation process has begun. Once the button is pressed, the inflation timer stops counting. The $V_u$ valve is closed, and the $V_f$ valve is opened, such that the syringe 412 is coupled with the balloon catheter. The plunger then moves in the reverse direction with a determined speed and for a determined distance to deflate the balloon. When deflation has completed, a corresponding indictor light may be displayed on the control panel.

The speeds and distances shown in FIG. 17A and FIG. 17B are exemplary only. Various other speeds and distances may be used in alternate embodiments. Speeds and distances may be predetermined by the inflation device in many instances. However, the user may be able to specify speeds and/or distances (for movement of the plunger) for certain operations. The user would do so through use of the control panel.

Figure 18:
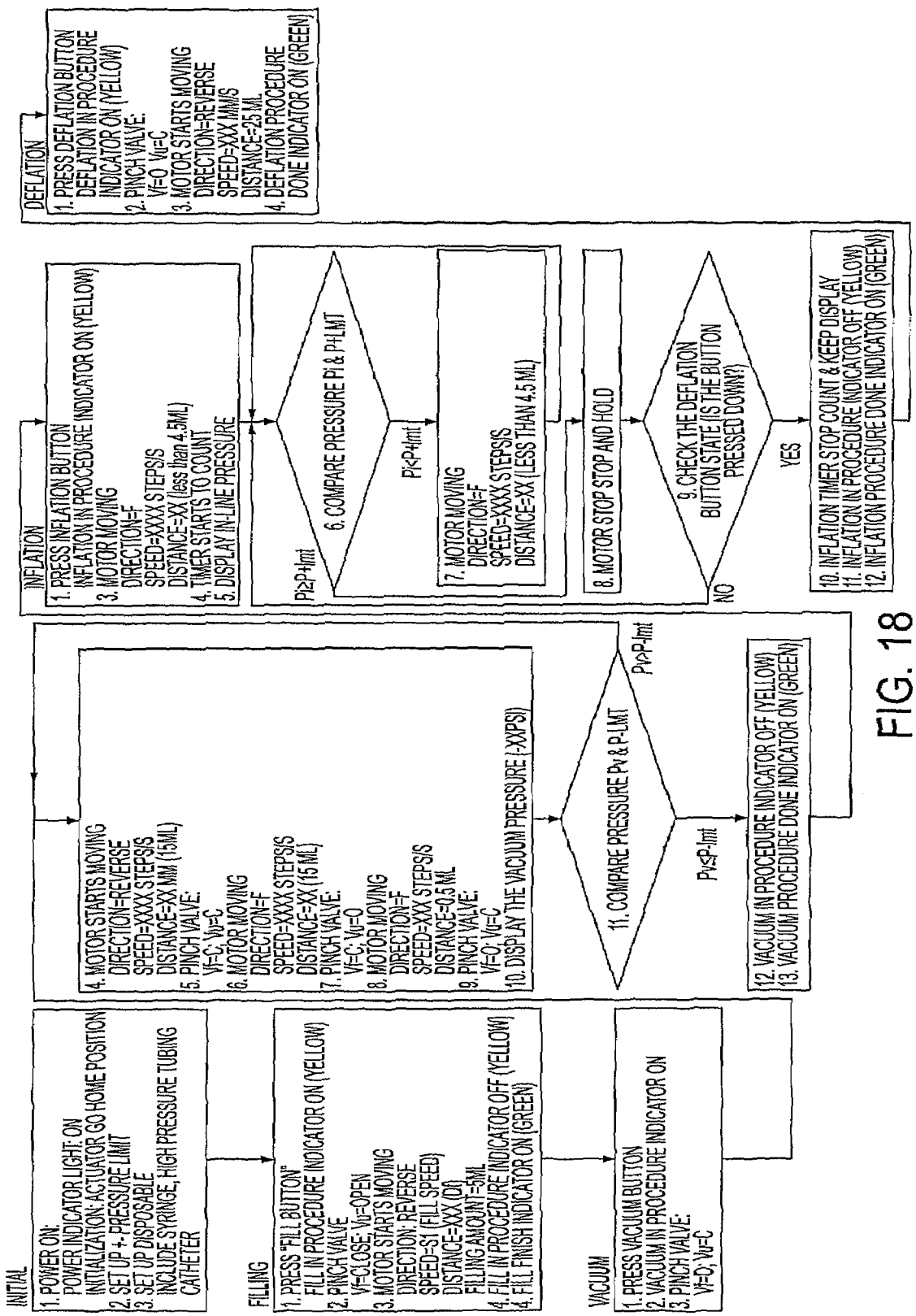
FIG. 18 is a flow diagram of methods that may be performed by the balloon inflation device shown in FIG. 16A, according to another embodiment.

FIG. 18 is a flow diagram of methods that may be performed by the balloon inflation device shown in FIG. 16A, according to another embodiment. Many of the procedures and actions shown and described in FIG. 18 are either identical or similar to those shown and described in FIGS. 17A and 17B. Some procedures and actions, however, are slightly different. For example, the procedure for pulling a vacuum shown in FIG. 18 is modified in certain regards. After the motor 422 causes the plunger to move in the reverse direction at a determined speed and for a determined distance, the pinch valves $V_f$ and $V_u$ are closed. The plunger then moves forward a determined distance, after which point the $V_u$ valve is opened. The motor 422 then causes the plunger to continue moving forward a determined distance, which may cause any existing air in the tubing to be pushed back into the fluid reservoir 400. The $V_f$ valve is then opened and the $V_u$ valve is closed. These acts are repeated until the pressure achieved is less than or equal to the specified negative pressure limit. At this point, the green status indicator light can be displayed to indicate that the vacuum procedure has been completed.

The inflation procedure shown in FIG. 18 also has some slight modifications to the procedure shown in FIG. 17B. For example, after the plunger begins moving forward a determined distance, the balloon inflation device continually compares the pressure of the balloon catheter (as may be calculated) with the Specified positive pressure limit. The plunger will continue to move forward incrementally for determined distances and with determined speeds until the pressure equals or exceeds the specified limit. Once this limit is reached, the motor causes the plunger to stop, so that the inflation pressure can be held. Once the deflation button has been pressed (which may be "Button 4" as shown in FIG. 16A), the inflation timer stops counting, and a green light may be displayed to indicate that inflation is complete. If the deflation button has not been pressed, the inflation timer continues to count, and the balloon inflation device continues to monitor the inflation pressure and compare it to the specified positive pressure limit. If, at some point, the pressure dips beneath the limit, the motor causes the plunger to move in the forward direction until the limit is again reached or exceeded. There are certain other slight modifications and differences between the procedures from FIG. 18 and those from FIGS. 17A and 17B, as are shown and described in these figures.

The foregoing description addresses embodiments encompassing the principles of various embodiments the present invention. The embodiments may be changed, modified and/or implemented using various types of arrangements. Those skilled in the art will readily recognize various modifications and changes that may be made to these embodiments without strictly following the exemplary embodiments and applications illustrated and described herein, and without departing from the scope of the invention, which is set forth in the following claims.

What is claimed is:

1. A method implemented by a powered inflation device to prepare a balloon catheter for use during a medical procedure, the method comprising:

closing a first valve of the inflation device to close off fluid communication between the balloon catheter and a pressurizing unit of the inflation device;

opening a second valve of the inflation device to allow fluid communication between the pressurizing unit and a fluid reservoir; and after closing the first valve and opening the second valve, and during a first motorized operation of the inflation device, moving a plunger of the pressurizing unit a first distance in a first direction to draw an amount of medical fluid from the fluid reservoir into the pressurizing unit;

after the first motorized operation of the inflation device:
closing the second valve to close off fluid communication between the pressurizing unit and the fluid reservoir,
opening the first valve to allow fluid communication between the pressurizing unit and the balloon catheter, and
during a second motorized operation of the inflation device, moving the plunger of the pressurizing unit a second distance in the first direction to remove an amount of air from the balloon catheter; and after the second motorized operation of the inflation device, and during a third motorized operation of the inflation device while the second valve is closed and the first valve is open, moving the plunger of the pressurizing unit a third distance in a second direction to inject the amount of medical fluid from the pressurizing unit into the balloon catheter to inflate a balloon located at a distal end of the balloon catheter, wherein the second direction is opposite to the first direction.

2. The method of claim 1, wherein the amount of medical fluid comprises an amount of contrast media.

3. The method of claim 2, wherein the amount of medical fluid further comprises an amount of diluent.

4. The method of claim 1, further comprising:
injecting the amount of air into a waste container.

5. The method of claim 1, further comprising:
during a fourth motorized operation of the inflation device, moving the plunger of the pressurizing unit in the first direction to deflate the balloon.

6. The method of claim 1, further comprising:
providing a control panel coupled to the inflation device to receive user input and to display information related to use of the inflation device.

7. The method of claim 6, further comprising:
receiving on the control panel user input to set an inflation rate or a deflation rate.

8. The method of claim 6, further comprising:
receiving on the control panel user input to set an inflation pressure limit.

9. The method of claim 6, further comprising:
displaying on the control panel a pressure-volume curve during inflation of the balloon at the distal end of the balloon catheter.

10. The method of claim 6, further comprising:
receiving on the control panel a single user input command to cause the inflation device to perform the acts of moving the plunger of the pressurizing unit to draw the amount of medical fluid into the pressurizing unit and to remove the amount of air from the balloon catheter during the first and second motorized operations, respectively.

11. The method of claim 1, further comprising:
after the second motorized operation of the inflation device, comparing a vacuum pressure associated with the balloon catheter with a negative pressure limit;
if the vacuum pressure is greater than the negative pressure limit, repeating at least the second motorized operation until the vacuum pressure is less than or equal to the negative pressure limit.

12. The method of claim 1, wherein the first valve is different from the second valve.

13. A powered inflation device to prepare a balloon catheter for use during a medical procedure, the inflation device comprising:
a motor; and
a pressurizing unit comprising a plunger, the pressurizing unit being operatively coupled to the motor and to a fluid reservoir;
wherein before a first operation, the inflation device closes a first valve of the inflation device to close off fluid communication between the pressurizing unit and the balloon catheter, and opens a second valve of the inflation device to allow fluid communication between the pressurizing unit and the fluid reservoir;
wherein, during the first operation, the motor causes the plunger of the pressurizing unit to move a first distance in a first direction to draw an amount of medical fluid from the fluid reservoir into the pressurizing unit;
wherein, after the first operation, the inflation device closes the second valve to close off fluid communication between the pressurizing unit and the fluid reservoir, and opens the first valve to allow fluid communication between the pressurizing unit and the balloon catheter;
wherein, after the first operation and during a second operation, the motor causes the plunger of the pressurizing unit to move a second distance in the first direction to remove an amount of air from a balloon catheter that is coupled to the inflation device; and
wherein, after the second operation and during a third operation, and while the second valve is closed and the first valve is open, the motor causes the plunger of the pressurizing unit to move a third distance in a second direction to inject the amount of medical fluid from the pressurizing unit into the balloon catheter to inflate a balloon located at a distal end of the balloon catheter, wherein the second direction is opposite to the first direction.

14. The inflation device of claim 13, wherein the amount of medical fluid comprises an amount of contrast media.

15. The inflation device of claim 14, wherein the amount of medical fluid further comprises an amount of diluent.

16. The inflation device of claim 13, further comprising a waste container.

17. The inflation device of claim 13, further comprising a control panel to receive user input and to display status information.

18. The inflation device of claim 13, wherein, during a fourth operation, the motor causes the plunger of the pressurizing unit to move in first direction to deflate the balloon.

19. The inflation device of claim 13, wherein the inflation device is a stand-alone device.

20. The inflation device of claim 13, wherein the inflation device is coupled to an angiographic injector system.

21. The inflation device of claim 20, wherein a common control panel is operable to control both the inflation device and the angiographic injector system.

22. The inflation device of claim 13,
wherein after the second motorized operation, the inflation device compares a vacuum pressure associated with the balloon catheter with a negative pressure limit, and
wherein if the vacuum pressure is greater than the negative pressure limit, the inflation device repeats at least the second motorized operation until the vacuum pressure is less than or equal to the negative pressure limit.

23. The inflation device of claim 13, wherein the first valve is different from the second valve.

* * * * *